United States Patent [19]
Ichimura et al.

[11] Patent Number: 5,345,306
[45] Date of Patent: Sep. 6, 1994

[54] METHOD AND APPARATUS FOR MEASURING SPECTRAL ABSORPTION IN AN OPAQUE SPECIMEN AND METHOD AND APPARATUS FOR MEASURING THE MICROSCOPIC ABSORPTION DISTRIBUTION

[75] Inventors: Tsutomu Ichimura, Dai 2 Green Haitsu-Zuiho 301, 1-1-20, Mukaiyama, Taihaku-ku, Sendai-shi, Miyagi 982; Fumio Inaba, Sendai, both of Japan

[73] Assignees: Research Development Corporation of Japan, Tokyo; Tsutomu Ichimura, Sendai, both of Japan

[21] Appl. No.: 704,142

[22] Filed: May 22, 1991

[30] Foreign Application Priority Data

May 22, 1990 [JP] Japan .................................. 2-133066
May 22, 1990 [JP] Japan .................................. 2-133067

[51] Int. Cl.⁵ .............................................. G01B 9/02
[52] U.S. Cl. .................................................... 356/346
[58] Field of Search ............... 356/346, 345, 361, 349; 250/341

[56] References Cited

U.S. PATENT DOCUMENTS 3,753,619 8/1973 Thorpe et al. ...................... 356/346
4,652,755 3/1987 Solomon et al. ................... 356/346

FOREIGN PATENT DOCUMENTS 0164680 12/1985 European Pat. Off. .
2191855 12/1987 United Kingdom .
8900281 1/1989 World Int. Prop. O. .
9000754 1/1990 World Int. Prop. O. .

OTHER PUBLICATIONS

"Nondestructive Refractive Index Characterization", GEC Journal of Research vol. 3, No. 3, 1985, Great Baddow Chemsfo, pp. 204–207; S. Ball.

Primary Examiner—Samuel A. Turner
Attorney, Agent, or Firm—Armstrong, Westerman, Hattori, McLeland & Naughton

[57] ABSTRACT

In the method of and apparatus for measuring a spectral absorption in an opaque specimen, a scattering specimen is illuminated with highly directional light of variable wavelength from a specific direction, thereby removing scattered rays as much as possible, and thus detecting the intensity of only parallel rays of a component transmitted or reflected in a specific direction (i.e., rectilinear component rays) by use of a highly directional detecting system, for example, a heterodyne light-receiving system, Michelson light-receiving system, highly directional optical system, etc. It is therefore possible to measure spectral absorption characteristics of a scattering specimen with high accuracy without picking up scattered light in other undesired directions nor other noise light. In addition, the measurement of the control is exceedingly simplified in comparison to the conventional method and thus the measurement is extremely facilitated. Thus, the method and apparatus of the present invention are suitable for measuring spectral absorption of a component transmitted or reflected in a specific direction in not only sparse heterogeneous systems having spatial resolving power, for example, suspensions, organic tissues, etc., but also dense translucent objects.

6 Claims, 23 Drawing Sheets

Ob Objective lens
SM Single-mode fiber

N.A ≃ 0.1        N.A ≃ 0.1

GL        SM

METHOD AND APPARATUS FOR MEASURING SPECTRAL ABSORPTION IN AN OPAQUE SPECIMEN AND METHOD AND APPARATUS FOR MEASURING THE MICROSCOPIC ABSORPTION DISTRIBUTION

BACKGROUND OF THE INVENTION

The present invention relates to a method of and apparatus for measuring spectral absorption in scattering objects, e.g., suspensions, powder, etc., and, more particularly, to a method of and apparatus for measuring spectral absorption characteristics of a component transmitted or reflected in a specific direction when a beam is applied to a specimen from a specific direction.

The present invention also relates to a method of and apparatus for measuring a microscopic absorption distribution of opaque specimens, e.g., biological specimens, and, more particularly, to a method of and apparatus for measuring a microscopic absorption distribution, wherein unnecessary scattered light is removed to improve the resolution so that it is possible to accurately measure absorption in a very small region of a specimen.

Since the discovery of X-rays, techniques of externally observing the inside of a living body (e.g., human body) without damaging it (i.e., a bloodless or non-destructive measuring method) have been strongly demanded and developed in the field of biology, particularly in the medical field. These techniques employ gamma rays and X-rays, which have the shortest wavelengths among the electromagnetic waves, and radio waves, which have the longest wavelengths among them. The technique that employs the former has already been put to practical use as X-ray CT, and the technique that employs the latter as NMR-CT (Magnetic Resonance Imaging, i.e., MRI).

On the other hand, fewer attempts have been made to apply spectroscopy that deals with the measurement and analysis of ultraviolet, visible, near infrared and infrared spectra, which is widely employed in the fields of physics and chemistry, to in vivo measurement. This is because biometry that employs light, particularly the one that utilizes the process of absorption or emission of light has many problems left unsolved in terms of "quantitativeness", which is the most basic matter. This is the reason why reproducibility is inferior and reliability is low in regard to the absolute values obtained in measurement that is conducted at the present time by using, for example, an apparatus that measures reflected spectra with a solid-state device, or a highly sensitive TV camera.

In a case where light is applied to a scattering object such as an organic tissue, if the light is received face to face at 180°, it is possible to take out rectilinearly propagating light to some extent. However, the spatial resolving power is not very high in the present state of art.

The difference in the spatial resolving power between X-rays and light cannot be made up in the present state of art. However, employment of light rays, particularly near infrared rays will enable imaging of a tissue oxygen concentration from the hemoglobin in the blood. These light rays will give information which is different from that obtained by other techniques such as NMR-CT and X-ray CT.

As for relatively thin tissues with a thickness of 3 to 5 cm, it is possible to detect light transmitted thereby. This means that "photo-roentgenography" can be used for diagnostic purposes. The women's breasts have relatively homogeneous tissues and hence readily transmit light, and it is easy to detect the light transmitted thereby (thickness: up to about 3 cm) owing to the configuration. For this reason, "photo-roentgenography" has been employed for a medical examination for breast cancer for a long time under the name of "diaphanography (lightscanning)".

Under these circumstances, the present inventor disclosed that a plane wave mixed in scattered light can be separated therefrom for observation by detecting only the 0-order spectrum (corresponding to the first dark ring of an Airy's disk) of the Fraunhofer diffraction image (Airy's disk) of the plane wave and, by so doing, most of the scattered light can be removed. See, for example, Japanese Patent Application Nos. 01-62898 (1989), 01-250034 (1989) and 02-77690 (1990). More specifically, when only a 0-order Fraunhofer diffraction pattern of a plane wave as signal light is to be detected, the degree of separation of incoherent scattered light from the plane wave is given by (scattering intensity)/(transmitted plane wave intensity) $\approx (\lambda/Dr)^2$ In other words, the larger the beam diameter or the entrance aperture diameter $Dr$ of a highly directional detecting system, e.g., a heterodyne light-receiving system, a Michelson light-receiving system, a highly directional optical system, etc., in comparison to the wavelength $\lambda$, the more the scattered light attenuates, and the more the scattered light can be separated from the plane wave. As one example of a highly directional optical system used to realize such observation, the present inventor proposed an optical system comprising two pinholes $P_1$ and $P_2$ which are spaced apart from each other, as shown in FIG. 27. This optical system is arranged such that 0-order light is detected by a detector 23 through the pinhole $P_2$. The present inventor also proposed a highly directional optical system comprising a hollow, straight, long and thin glass fiber 35 the inner wall surface of which is coated with a light absorbing material, e.g., carbon, as shown in FIG. 28. Further, the present inventor proposed various highly directional optical systems such as those shown in FIGS. 29 to 36: a highly directional optical system (FIG. 29) comprising an objective lens Ob and a pinhole P that is disposed on the focal plane thereof to pass only a 0-order Fraunhofer diffraction pattern formed by the objective lens Ob; a highly directional optical system (FIG. 30) comprising a graded-index lens GL and a pinhole P (similar to that shown in FIG. 29) that is disposed on the focal plane at one end of the graded-index lens GL; a highly directional optical system (FIGS. 31 and 32) in which the pinhole P is replaced with an optical fiber SM that functions in the same way as the pinhole P; a highly directional optical system (FIGS. 32 and 35) in which an objective lens Ob2 which is similar to an objective lens Ob1 at the entrance side is disposed at the exit side of the pinhole P or the optical fiber SM in the above-described highly directional optical systems; and a highly directional optical system (FIGS. 34 and 36) in which a graded-index lens GL2 which is similar to a graded-index lens GL1 at the entrance side is disposed at the exit side of the pinhole P or the optical fiber SM.

Incidentally, there are known methods of measuring absorption in opaque specimens, for example, the opal glass method in which a rectilinear component and a transmission and scattering component of a specimen that causes scattering are uniformly scattered by use of opal glass to measure a transmission integral extinction of the specimen [see, for example, Kazuo Shibata "Photobiology Series: Introduction to Spectral Measurement", pp.62-82 (Jun. 20, 1976, Kyoritsu Shuppan K. K.)]. Heterogeneous systems such as suspensions of particles, for example, cells, granules, solid powder, etc. absorb and scatter light, in general. Accordingly, it is difficult to obtain only absorption wavelength characteristics of such heterogeneous systems. For this reason, it is conventional practice to obtain a quantity with which real absorption wavelength characteristics can be approximated. More specifically, a transmission integral extinction is obtained to replace absorption. The transmission integral extinction is the cologarithm of the ratio of a bundle of light rays attenuated by both absorption and scattering to the incident light rays, which is not coincident with absorption characteristics, in general. In order to enable the transmission integral extinction to be approximated to real absorption characteristics as much as possible, if parallel transmitted rays and scatteringly transmitted rays are detected at the same capturing rate by a detector, the effect of scattering on the ratio of the light rays becomes small. As a method for this purpose, the opal glass method has been put to practical use. In addition, the transmission integrating sphere method, photoelectric surface contact method, etc. have been put to practical use as methods of minimizing the effect of scattering by capturing the entire transmitted rays comprising parallel transmitted rays and scatteringly transmitted rays. A method that utilizes both the contact and scattering methods jointly has also been employed as an intermediate method between the detection of parallel transmitted light rays and scatteringly transmitted light rays at the same capturing rate and the detection of the entire transmitted light rays.

Meantime, a measuring method such as that shown in FIG. 37 has heretofore been employed to measure a microscopic absorption distribution in a specimen that causes scattering. More specifically, light from a light source that emits light over a wide spectral range is passed through an interferometer for Fourier spectroscopy and then sent to either a transmission optical path or a reflection optical path through a transmission/reflection switching mirror. If the transmission optical path is selected, the illuminating light is condensed to a very small point on a specimen placed on a specimen table through a lower Cassegrain system that functions as a condenser lens. Light that is transmitted through the measuring point and light that is forwardly scattered at the measuring point are focused on an aperture through an upper Cassegrain system that functions as an objective lens, and the light that passes through the aperture is made incident on a detector to measure absorption characteristics at the measuring point. Thus, it is possible to measure a transmission microscopic absorption distribution in the specimen by repeating measurement similar to the above with the specimen table being scanned in directions X and Y. If the switching mirror is changed over to the reflection optical path, the illuminating light is condensed to a point on the specimen through the upper Cassegrain system, and light that is reflected and scattered backwardly from the measuring point is focused on the aperture through the same upper Cassegrain system. Thus, a reflection microscopic absorption distribution in the specimen can be measured in the same way as the above.

FIG. 38 shows another conventional microspectroscopic method that employs a combination of an optical microscope and a spectrophotometer to observe an absorption spectrum of a very small region. Light from a light source 1 is formed into monochromatic light through a spectroscope $m_0$ to illuminate a diaphragm (pinhole) p. With the diaphragm p defined as a light source of a microscope system, light is passed through an illuminating microscope $m_1$. In consequence, a reduced image of the diaphragm p is formed on a specimen plane s. This image is enlarged through another microscope $m_2$ and led to a detector d. If a specimen is placed at the position s where the reduced image of the diaphragm is formed, it is possible to measure absorbance of only a local region in the specimen.

Incidentally, if the same measuring method that is used for a specimen that causes no scattering is employed to obtain an absorption spectrum of a specimen that causes scattering, the effect of scattering is large, so that it is impossible to obtain an accurate absorption spectrum. As techniques of measuring absorption in opaque specimens, methods wherein a transmission integral extinction is measured by use of opal glass, an integrating sphere, etc., are known, as described above.

The above-described conventional methods, however, suffer from problems stated below: (1) the opal glass method involves the disadvantage that the light scattering power undesirably changes in accordance with wavelength; (2) the transmission integrating sphere method involves the disadvantage that a white reflecting material in the integrating sphere greatly decreases in reflectivity at a short wavelength, particularly near the ultraviolet region, even in the case of MgO powder, which is known as the best reflecting material, so that no reliable data can be obtained; (3) the photoelectric surface contact method that employs two detectors involves difficulty in obtaining the same wavelength sensitivity characteristics, whereas the photoelectric surface contact method that employs a single detector involves difficulty in installing a specimen and a control within a limited space; and (4) the method that employs both the contact and scattering methods jointly suffers from the problem that it is necessary to properly select the size of a specimen and the distance and size of the detector, although it is superior to the former three methods.

In addition, the four conventional methods involve the common disadvantage that there are cases where a transmission integral extinction measured cannot be approximated to the absorption wavelength of suspended particles. More specifically, as the intensity of reflected rays increases, it becomes impossible to make approximation. When the scattering spatial pattern that is formed by a specimen depends upon wavelength, the wavelength change of scatteringly transmitted rays becomes different from that of the scatteringly reflected rays, so that no approximation can be made. In addition, it is difficult to perform absorption measurement that provides spatial resolving power such as specifies a location of absorption. Although the conventional methods are usable for measurement of absorption in sparse heterogeneous systems such as dilute suspensions, these methods cannot be applied to measurement of absorption in dense translucent objects such as biological specimens when scattering is so strong that the relationship of Kubelta-Munk is valid.

The microspectroscopic measuring method for infrared region that employs a Fourier spectroscope and the microspectroscopic measuring method for visible region that employs a diffraction grating spectroscope, which have been described above, have no measures taken to deal with opaque specimens that cause scattering and therefore involve large errors in the measurement of such specimens, so that no reliable data can be obtained. In other words, since unnecessary scattered light mixes in from the surroundings including the front and rear of the measuring point, it is impossible to measure accurate absorption characteristics. In addition, since Fraunhofer diffraction patterns other than the 0-order diffraction pattern enter the objective lens, the resolution is limited. The measuring method that is a simple combination of the measuring method employing opal glass or an integrating sphere, developed as a method of measuring absorption in opaque specimens, and the microspectroscopic measuring method involves the problem that the detected signal light is weak so that it is difficult to effect measurement, and it cannot therefore be put to practical use. Even if the detection sensitivy is improved markedly, since the method that employs opal glass or an integrating sphere is merely an approximation method, it cannot be used for a specimen for which approximation cannot be made when the intensity of reflected rays is high or when the wavelength change of scatteringly transmitted rays is the same as that of scattering reflected rays, due to large errors. Even if such a measuring method can be used, the spatial resolving power is deteriorated. Thus, there is no proper measuring method for an absorption spectrum in a very small region of an opaque specimen that causes scattering in the present state of art.

SUMMARY OF THE INVENTION

In view of the above-described circumstances, it is a first object of the present invention to provide a method of and apparatus for measuring spectral absorption characteristics by removing scattered light rays in a scattering object, for example, a suspension, organic tissue, etc, as much as possible and capturing parallel rays of a component transmitted or reflected in a specific direction (i.e., rectilinear component rays).

It is a second object of the present invention to provide a method of and apparatus for measuring a microscopic absorption distribution, wherein unnecessary scattered light is removed to improve the resolution so that it is possible to accurately measure absorption in a very small region of an opaque specimen, for example, an organic tissue.

To attain the first object, the present invention provides a method of measuring spectral absorption in an opaque specimen, comprising the steps of: illuminating a scattering specimen with highly directional light of variable wavelength from a specific direction; capturing parallel rays of a component transmitted or reflected in a specific direction (i.e., rectilinear component rays); and detecting the intensity of only the parallel rays by use of a highly directional detecting system, thereby measuring spectral absorption characteristics of the specimen.

The specific direction in which the intensity is detected by the highly directional detecting system may be either a direction for detection of light transmitted by the specimen or a direction for detection of light reflected and scattered by the specimen.

In addition, the present invention provides a first apparatus for measuring spectral absorption in an opaque specimen, comprising: a monochromatic light source capable of varying the wavelength of light emitted therefrom; means for dividing the light from the light source into two light beams; means for shifting the frequency of incident light, the shift means being provided in the optical path of one of the two light beams; a scattering specimen disposed in the optical path of the other light beam; means for combining together highly directional light emerging from the frequency shift means and a beam of parallel rays (rectilinear component rays) emerging from the specimen in a specific direction and projecting the resulting composite light in the same direction; and means for converting the composite light from the beam combining means into an electric signal and detecting the intensity of only an AC component which is equal to the shifted frequency.

In addition, the present invention provides a second apparatus for measuring spectral absorption in an opaque specimen, comprising: a monochromatic light source capable of varying the wavelength of light emitted therefrom; means for dividing the light from the light source into two light beams; means for changing the optical path length at a predetermined speed, the optical path length changing means being provided in the optical path of one of the two light beams; a scattering specimen disposed in the optical path of the other light beam; means for combining together highly directional light emerging from the optical path length changing means and a beam of parallel rays (rectilinear component rays) emerging from the specimen in a specific direction and projecting the resulting composite light in the same direction; and means for converting the composite light from the beam combining means into an electric signal and detecting the intensity of only an AC component of a frequency corresponding to the optical path length changing speed.

In addition, the present invention provides a third apparatus for measuring spectral absorption in an opaque specimen, comprising: a monochromatic light source capable of varying the wavelength of light emitted therefrom; a scattering specimen disposed in the optical path of light emitted from the light source; a highly directional optical system for extracting parallel rays (rectilinear component rays) emerging from the specimen in a specific direction; and means for detecting the intensity of light extracted by the highly directional optical system.

The third measuring apparatus may further comprise switching means which is provided in the optical path of light emitted from the light source to switch over two optical paths from one to the other, the two optical paths being coaxial but opposite to each other in the direction of travel of light, the highly directional optical system being disposed in the coaxial optical paths, and the scattering specimen being disposed at one side of the highly directional optical system, thereby taking out light transmitted through the specimen in a specific direction or light reflected and scattered by the specimen in a specific direction from the other side of the highly directional optical system.

In any of these apparatus, transmission integral extinction can be obtained by defining the intensity of light transmitted through the specimen or reflected thereby in a specific direction as a signal light intensity and defining the whole or part of the illuminating light as a reference light intensity. When a highly directional detecting system is employed, the intensity of part of the illuminating light beam is detected to obtain a reference light intensity, and a light intensity that is detected by use of the highly directional detecting system is defined as a signal intensity, thereby obtaining a transmission integral extinction by use of the reference light intensity and the signal intensity. When a heterodyne light-receiving system or a Michelson light-receiving system is employed, with light from the scattering specimen being cut off, the intensity of highly directional light emerging from the frequency shift means or the optical path length changing means is detected to obtain a reference light intensity, and light obtained from the beam combining means is converted into an electric signal and an AC component which is equal to the shifted frequency or an AC component of a frequency corresponding to the optical path length changing speed is defined as a signal intensity obtained from the specimen, thereby obtaining a transmission integral extinction by use of the reference light intensity and the signal intensity.

To attain the second object, the present invention provides a method of measuring a microscopic absorption distribution in an opaque specimen, comprising the steps of: illuminating a very small measuring point on a specimen with condensed light of high directivity; converting light diverging from the measuring point into parallel rays; detecting the intensity of only the parallel rays by use of a highly directional detecting system; and repeating the detecting operation with the specimen being scanned relative to the condensed light, thereby measuring absorption distribution characteristics of the specimen.

In this case, if the illuminating region is restricted by disposing a pinhole in extremely close proximity to the measuring point, the pinhole being smaller than the size of a 0-order Fraunhofer diffraction pattern of the condensed light, it is possible to effect microscopic absorption distribution measurement of higher resolution.

It is also possible to effect microscopic absorption distribution measurement by use of light of variable wavelength as the light of high directivity.

If an excited light cut-off filter is inserted in the optical path that extends from the measuring point to the detecting system to cut off light of the same wavelength as that of the illuminating light, it is possible to measure a microscopic fluorescence distribution in the specimen.

The arrangement may be such that the intensity of part of the light beam applied to the specimen is detected to obtain a reference light intensity, and a light intensity that is detected by use of the highly directional detecting system is defined as the intensity of signal light from the specimen, thereby obtaining a transmission integral extinction by use of the reference light intensity and the signal intensity.

In addition, the present invention provides a first apparatus for measuring a microscopic absorption distribution in an opaque specimen, comprising: a monochromatic light source capable of varying the wavelength of light emitted therefrom; means for dividing the light from the light source into two light beams; means for shifting the frequency of incident light, the shift means being provided in the optical path of one of the two light beams; a confocal optical system comprising two convergent optical systems, the confocal optical system being disposed in the other optical path; a specimen disposed at a position where light is condensed by the confocal optical system, the specimen being capable of being scanned relative to the confocal optical system; means for combining together highly directional light emerging from the frequency shift means and light diverging from a measuring point on the specimen and converted into parallel rays by the confocal optical system and projecting the resulting composite light in the same direction; and means for converting the composite light from the beam combining means into an electric signal and detecting the intensity of only an AC component which is equal to the shifted frequency.

In addition, the present invention provides a second apparatus for measuring a microscopic absorption distribution in an opaque specimen, comprising: a monochromatic light source capable of varying the wavelength of light emitted therefrom; means for dividing the light from the light source into two light beams; means for changing the optical path length at a predetermined speed, the optical path length changing means being provided in the optical path of one of the two light beams; a confocal optical system comprising two convergent optical systems, the confocal optical system being disposed in the other optical path; a specimen disposed at a position where light is condensed by the confocal optical system, the specimen being capable of being scanned relative to the confocal optical system; means for combining together highly directional light emerging from the optical path length changing means and light diverging from a measuring point on the specimen and converted into parallel rays by the confocal optical system and projecting the resulting composite light in the same direction; and means for converting the composite light from the beam combining means into an electric signal and detecting the intensity of only an AC component of a frequency corresponding to the optical path length changing speed.

In addition, the present invention provides a third apparatus for measuring a microscopic absorption distribution in an opaque specimen, comprising: a monochromatic light source capable of varying the wavelength of light emitted therefrom; a confocal optical system comprising two convergent optical systems, the confocal optical system being disposed in the optical path of light emitted from the light source; a specimen disposed at a position where light is condensed by the confocal optical system, the specimen being capable of being scanned relative to the confocal optical system; a highly directional optical system arranged to extract only light traveling in the direction of travel of light diverging from a measuring point on the specimen and converted into parallel rays by the confocal optical system; and means for detecting the intensity of light extracted by the highly directional optical system.

The third measuring apparatus may further comprise: switching means which is provided in the optical path of light emitted from the light source to switch over two optical paths from one to the other, the two optical paths being coaxial but opposite to each other in the direction of travel of light; the confocal optical system being disposed in the coaxial optical paths; means for taking out light transmitted through the specimen or light reflected and scattered by the specimen, the means being disposed at one side of the confocal optical system; and the highly directional optical system being disposed in the rear of the light taking-out means. By so doing, it is possible to measure absorption distribution characteristics of both light transmitted through the specimen and light reflected and scattered thereby with a single apparatus.

In addition, the present invention provides a fourth apparatus for measuring a microscopic absorption distribution in an opaque specimen, as a modification of the first measuring apparatus, which comprises: a monochromatic light source capable of varying the wavelength of light emitted therefrom; means for dividing the light from the light source into two light beams; means for shifting the frequency of incident light, the shift means being provided in the optical path of one of the two light beams; a first convergent optical system disposed in the other optical path to illuminate a very small measuring point on a specimen with condensed light of high directivity; a specimen disposed at a position where light is condensed by the first convergent optical system, the specimen being capable of being scanned relative to the first convergent optical system; a second convergent optical system arranged to illuminate the specimen with highly directional light emerging from the frequency shift means in the form of the same convergent spherical wave as that obtained from the first convergent optical system; means for combining together light emerging from the frequency shift means and light diverging from the measuring point on the specimen and converted into parallel rays by the second convergent optical system and projecting the resulting composite light in the same direction; and means for converting the composite light from the beam combining means into an electric signal and detecting the intensity of only an AC component which is equal to the shifted frequency.

In any of these apparatus, transmission integral extinction can be obtained by defining the intensity of parallel rays (rectilinear component rays) transmitted through the specimen or parallel rays (rectilinear component rays) reflected thereby in a specific direction as a signal light intensity and defining the whole or part of the illuminating light as a reference light intensity. When a highly directional detecting system is employed, the intensity of part of the illuminating light beam is detected to obtain a reference light intensity, and a light intensity that is detected by use of the highly directional detecting system is defined as a signal intensity, thereby obtaining a transmission integral extinction by use of the reference light intensity and the signal intensity. When a heterodyne detecting system or a Michelson detecting system is employed, with light from the scattering specimen being cut off, the intensity of only highly directional light emerging from the frequency shift means or the optical path length changing means is detected to obtain a reference light intensity, and a beat component in the heterodyne detecting system or the Michelson detecting system is defined as a signal light intensity, thereby obtaining a transmission integral extinction by use of the reference light intensity and the signal light intensity.

Thus, according to the method of and apparatus for measuring a spectral absorption in an opaque specimen, a scattering specimen is illuminated with highly directional light of variable wavelength from a specific direction, thereby removing scattered rays as much as possible, and thus detecting the intensity of only parallel rays of a component transmitted or reflected in a specific direction (i.e., rectilinear component rays) by use of a highly directional detecting system, for example, a heterodyne light-receiving system, Michelson light-receiving system, highly directional optical system, etc. It is therefore possible to measure spectral absorption characteristics of a scattering specimen with high accuracy without picking up scattered light in other undesired directions nor other noise light. In addition, the measurement of the control is exceedingly simplified in comparison to the conventional method and thus the measurement is extremely facilitated. Thus, the method and apparatus of the present invention are suitable for measuring spectral absorption of a component transmitted or reflected in a specific direction in not only sparse heterogeneous systems having spatial resolving power, for example, suspensions, organic tissues, etc., but also dense translucent objects.

According to the method of and apparatus for measuring a microscopic absorption distribution in an opaque specimen, a very small measuring point on a specimen is illuminated with a condensed light of high directivity, and light that diverges from the measuring point is converted into parallel rays, or left as it is in the form of a spherical wave, and then detected by use of a highly directional detecting system, for example, a heterodyne light-receiving system, Michelson light-receiving system, highly directional optical system, etc. It is therefore possible to measure absorption in a very small region of a specimen with high resolution without picking up scattered light from the surroundings of the measuring point nor other noise light. Thus, the method and apparatus of the present invention are suitable for measurement of a microscopic absorption distribution in an opaque specimen, for example, an organic tissue.

Still other objects and advantages of the invention will in part be obvious and will in part be apparent from the specification.

The invention accordingly comprises the features of construction, combinations of elements, and arrangement of parts which will be exemplified in the construction hereinafter set forth, and the scope of the invention will be indicated in the claims.

DESCRIPTION OF THE PREFERRED EMBODIMENTS

Heterodyne light-receiving system has heretofore been known as a means for detecting coherent light with high sensitivity. As shown schematically in FIG. 1, a heterodyne light-receiving system 3 is arranged such that light of a specific frequency $\omega_1$ from a laser 1 is split by a beam splitter BS into two light beams, that is, one that travels rectilinearly and the other that is reflected from the beam splitter BS, and a specimen S is inserted in the path of the rectilinear light. The reflected light is passed via mirrors M1 and M2 and then combined with the rectilinear light by a half-mirror HM, and the resulting composite light is then photoelectrically converted in a detector 2. If a frequency shifter AO, for example, an ultrasonic light modulator, is inserted in the path of the reflected light to shift the frequency to $\omega_2$, a beat signal of an observable frequency, i.e., a difference between the two frequencies $\omega_1$ and $\omega_2$, appears from the detector 2. The intensity of the AC component of the beat signal is proportional to the transmittance of the specimen S. Accordingly, it is possible to detect a weak signal transmitted through the specimen S. In the heterodyne light-receiving system 3, the light component that is scattered by the specimen S in a direction different from the direction of the reflected light (i.e., the light of frequency $\omega_2$; hereinafter referred to as "reference light" in some cases) does not overlap with the reference light on the detecting surface of the detector 2, so that no beat signal is generated thereby, and it is detected as merely a DC component. Thus, the heterodyne light-receiving system 3 functions as a highly directional detecting system which is capable of readily removing such a scattering component and detecting only a light component that travels in the same direction as the reference light as well as detecting a weak signal as described above. Accordingly, the present invention makes use of the nature of the heterodyne light-receiving system 3 as a highly directional detecting system.

Figure 4:
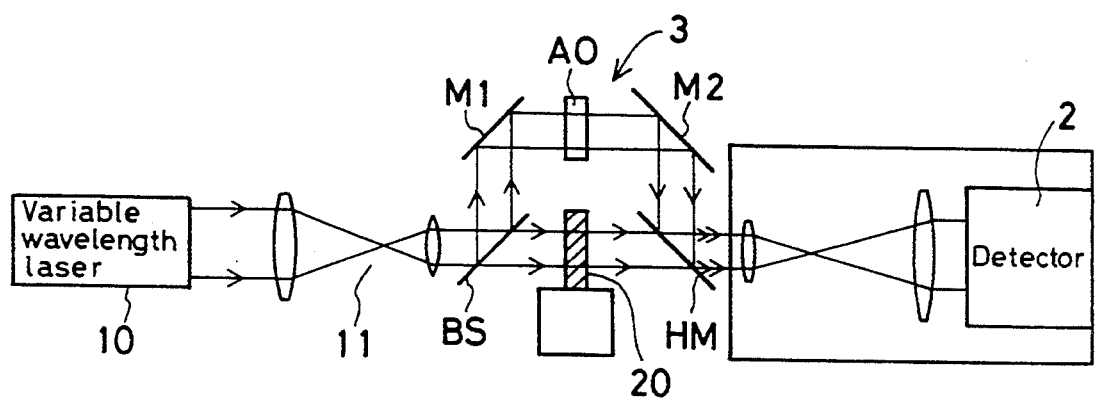
FIGS. 4 and 5 show the arrangements of embodiments of the spectral absorption measuring apparatus employing a heterodyne light-receiving system according to the present invention, which are applied to a transmitting specimen and a reflecting specimen, respectively.

In addition, Michelson light-receiving system is well known as a means capable of detecting a very small change in the refractive index or the like. In a Michelson light-receiving system 2, as shown in FIG. 4, light from a laser 1 is split by a beam splitter BS into two light beams, one of which is reflected from mirrors M1 and M2 while being transmitted through a specimen S inserted in the path of the reflected light, and the transmitted light is combined with rectilinear light (described later) by a half-mirror HM. The rectilinear light (hereinafter referred to as "reference light") that is transmitted through the beam splitter BS passes through the half-mirror HM and strikes upon a moving mirror M that is moved as shown by the double-headed arrow in the figure. The light is reflected in the reverse direction and combined by the half-mirror HM with the light transmitted through the specimen S, and the resulting composite light is photoelectrically converted in a detector 2. The detector 2 outputs a signal upon which is superposed an interference signal the frequency of which corresponds to the speed of the moving mirror M. The intensity of the AC component of the output signal is proportional to the transmittance of the specimen S, and the phase of the signal depends upon the thickness or refractive index of the specimen S. The Michelson light-receiving system 4 is also capable of detecting a very small change in the refractive index or the like in the same way as the above-described heterodyne light-receiving system 3. In addition, since the light component that is scattered by the specimen S in a direction different from the direction of the reference light does not overlap with the reference light on the detecting surface of the detector 2, no beat signal is generated thereby and the scattered light is detected as merely a DC component. Thus, the Michelson light-receiving system 4 also functions as a highly directional detecting system which is capable of readily removing such a scattering component and detecting only a light component that travels in the same direction as the reference light as well as detecting a weak signal as described above. Accordingly, the present invention makes use of the nature of the Michelson light-receiving system 4 as a highly directional detecting system.

Incidentally, it can be said that both the heterodyne light-receiving system 3 and the Michelson light-receiving system 4 detect the intensity of the light transmitted or scattered by the specimen S on the basis of the same principle. This point will be briefly explained below. Assuming that the reference light which is to be combined is $V_2$ and the light transmitted or scattered by the specimen S (hereinafter referred to as "specimen light" in some cases) is $V_1$, these two light waves are expressed as follows:

$$V_1 = A_1 \exp[-i(\omega_1 t + \Phi_1)]$$

$$V_2 = A_2 \exp[-i(\omega_2 t + \Phi_2)]$$

When these two light waves $V_1$ and $V_2$ are observed (detected) in a superposed state, the detected signal S is given by $$S = |V_1 + V_2|^2 = V_1 \cdot V_1^* + V_2 \cdot V_2^* + V_1 \cdot V_2^* + V_1^* \cdot V_2$$

Because $$V_1 \cdot V_1^* = A_1^2, V_2 \cdot V_2^* = A_2^2$$

and $$V_1 \cdot V_2^* = A_1 A_2 \exp[-i(\omega_1 - \omega_2)t - i(\Phi_1 - \Phi_2)]$$

$$V_1^* \cdot V_2 = A_1 A_2 \exp[+i(\omega_1 - \omega_2)t + i(\Phi_1 - \Phi_2)]$$

$$V_1 \cdot V_2^* + V_1^* \cdot V_2 = 2A_1 A_2 \cos[(\omega_1 - \omega_2)t + (\Phi_1 - \Phi_2)]$$

the detected signal S is given by $$S = A_1^2 + A_2^2 + 2A_1 A_2 \cos[(\omega_1 - \omega_2)t + (\Phi_1 - \Phi_2)]$$

Since $\omega_2 = \omega_1 - \Delta\omega$ and $\Phi_1 = \Phi_2$ are valid in the heterodyne light-receiving system 3, the detected signal S is given by $$S = A_1^2 + A_2^2 + 2A_1 A_2 \cos \Delta\omega t$$

Thus, the amplitude $A_1$ of the specimen light $V_1$ can be known from the size of the AC component of the detected signal.

Similarly, since $\omega_1 = \omega_2$ and $\Phi_2 = \Phi_1 + kt$ in the Michelson light-receiving system 4, the detected signal S is given by $$S = A_1^2 + A_2^2 + 2A_1 A_2 \cos kt$$

Thus, it is possible to obtain a signal similar to that in the case of the heterodyne light-receiving system 3. More specifically, the heterodyne light-receiving system 3 and the Michelson light-receiving system 4 similarly enable the amplitude $A_1$ of the specimen light $V_1$ to be known from the size of the AC component of the detected signal.

Figure 3:
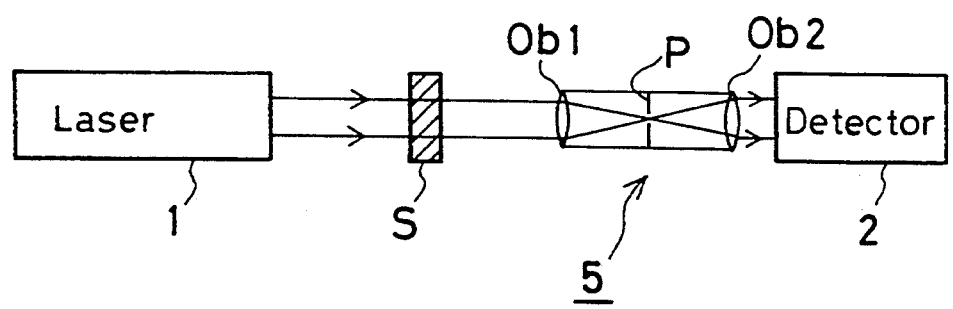
FIG. 3 shows the arrangement of a typical highly directional optical system as still another highly directional detecting system.

According to the present invention, the heterodyne light-receiving system 3 and the Michelson light-receiving system 4 are employed as a highly directional detecting system, and in addition to them, the highly directional optical systems exemplarily shown in FIGS. 26 to 36 are employed. Further, it is also possible in the present invention to employ a multiple beam highly directional optical system which comprises a bundle of such highly directional optical systems. For details, see the above-mentioned Japanese Patent Application No. 02-77690 (1990). FIG. 3 shows a highly directional optical system 5 as a representative of those highly directional optical systems, which comprises an objective lens Ob1 on the incidence side, a pinhole P that is disposed on the focal plane of the objective lens Ob1 to pass only a 0-order Fraunhofer diffraction pattern formed by the objective lens Ob1, and a similar objective lens Ob2 that is disposed so that its front focal point is coincident with the pinhole P (the illustrated highly directional optical system 5 is the same as the optical system shown in FIG. 33). However, it should be noted that the highly directional optical system 5 is not necessarily limitative to that shown in FIG. 3.

Opaque specimens which may be first objects of the spectral absorption measurement in the present invention are not those which block incident light completely and do not transmit it forwardly, but sparse heterogeneous systems such as dilute suspensions, e.g., biological specimens, and also specimens such as dense translucent biological specimens, in which substantially no light is transmitted directly therethrough without being scattered, but light that is multiple-scattered forwardly by scattering fine particles in the specimen emerges therefrom. It is a matter of course that a specimen which transmits light directly therethrough can be employed as an object of the measurement. Second objects of the measurement in the present invention are those which cut off the incident light substantially completely and reflect as well as scatter it only backwardly, such as powder specimens. The former specimens will hereinafter be referred to as "transmitting specimens", and the latter specimens as "reflecting specimens".

One embodiment of the method of and apparatus for measuring spectral absorption characteristics of an opaque specimen according to the present invention will be described below.

Figure 5:
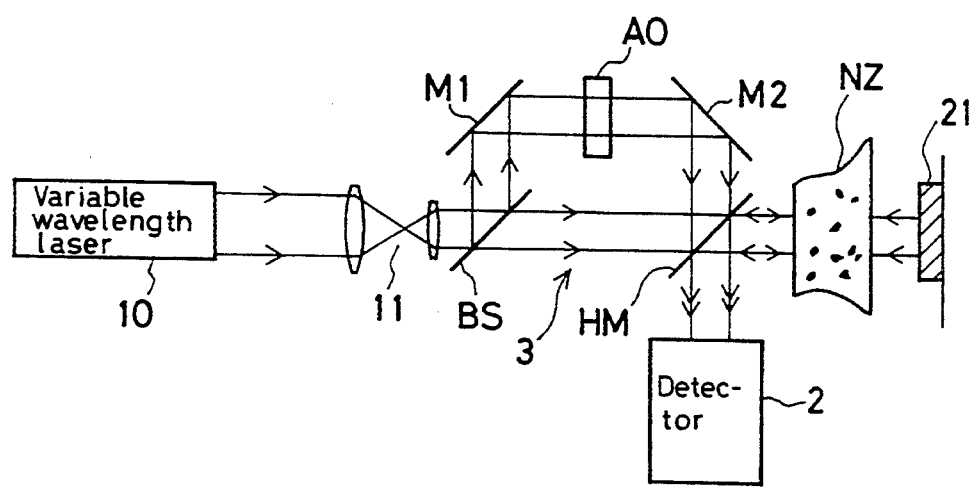
Figure 6:
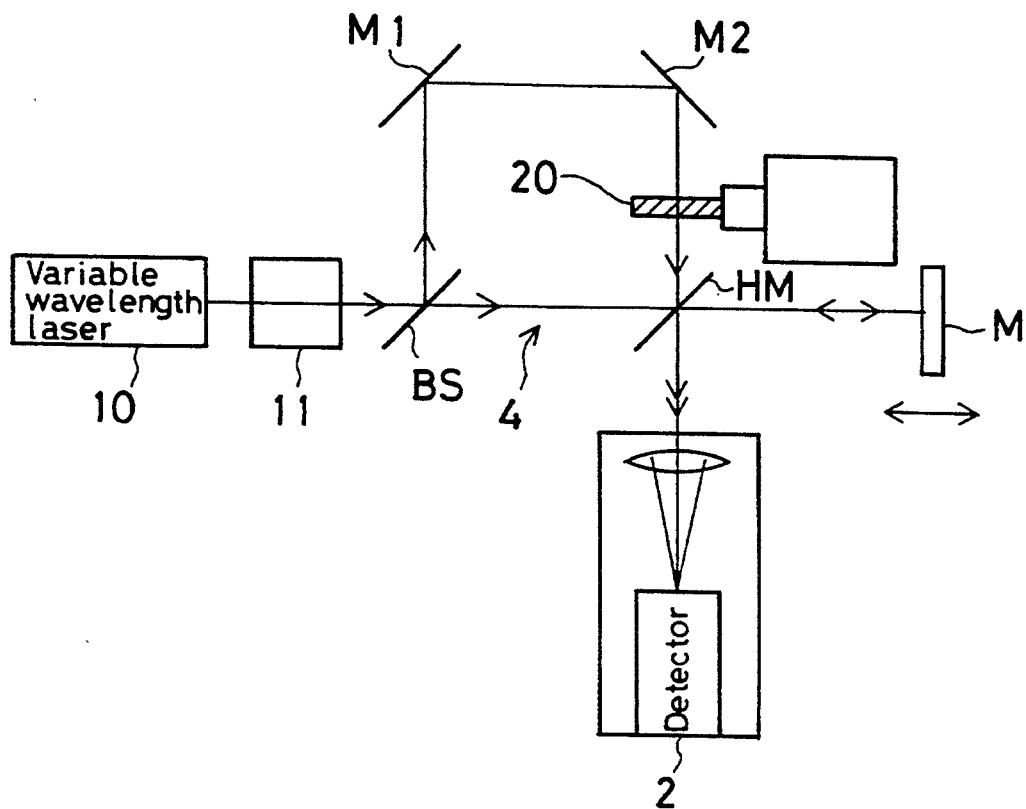
FIGS. 6 and 7 show the arrangements of embodiments of the spectral absorption measuring apparatus employing a Michelson light-receiving system according to the present invention, which are applied to a transmitting specimen and a reflecting specimen, respectively.
Figure 7:
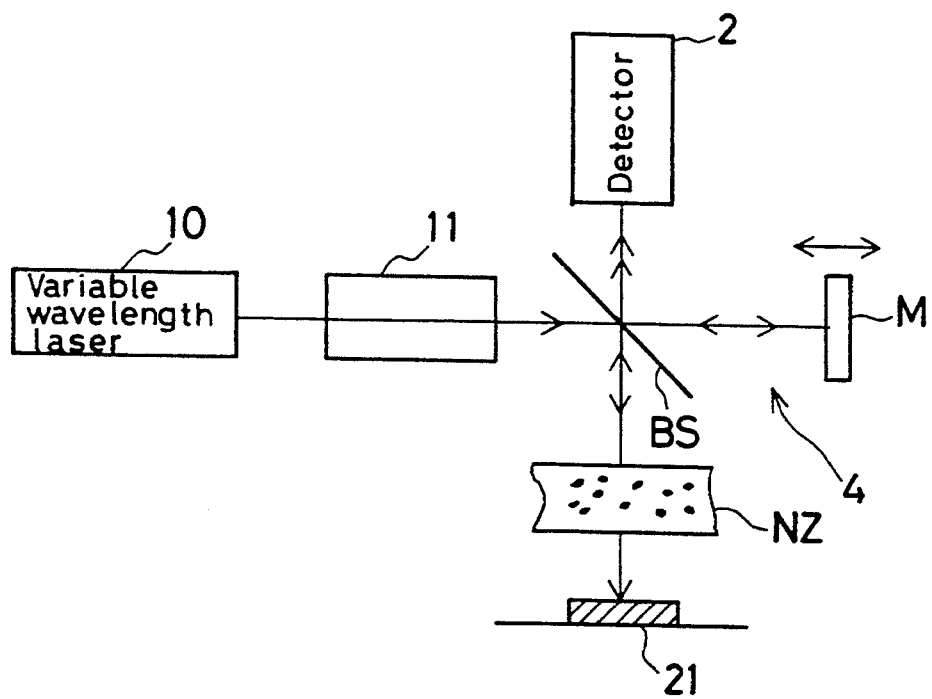
Figure 8:
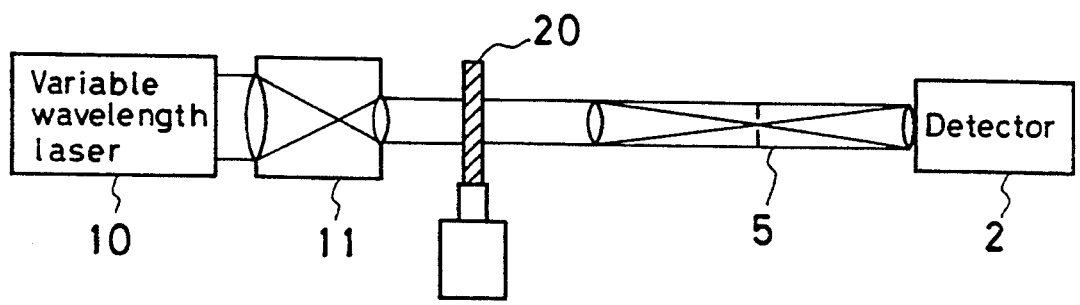
FIGS. 8 and 9 show the arrangements of embodiments of the spectral absorption measuring apparatus employing a highly directional optical system according to the present invention, which are applied to a transmitting specimen and a reflecting specimen, respectively.

FIGS. 4, 6 and 8 schematically show apparatuses for measuring spectral absorption characteristics of a transmitting specimen 20, and FIGS. 5, 7 and 9 to 11 schematically show apparatuses for measuring spectral absorption characteristics of a reflecting specimen 21.

The measuring apparatus that is shown in FIG. 4 employs the heterodyne light-receiving system 3 as a highly directional detecting system to take out only light that is scattered in a specific forward direction by the transmitting specimen 20, thereby measuring spectral absorption characteristics of the specimen 20. For such measurement, a variable wavelength laser 10 that can continuously emit monochromatic light sweepingly over a wide spectral range is employed as a monochromatic light source. A beam converter 11 is disposed in front of the laser 10 to convert a beam of light emitted from the laser 10 into a beam of parallel rays having a proper diameter. The light beam emerging from the beam converter 11 is split by a beam splitter BS into two light beams, that is, rectilinear light and reflected light. The rectilinear light strikes upon the transmitting specimen 20, in which it is subjected to multiple scattering and thus scattered forwardly in an isotropic manner, in general. In the forward scattered light, slight parallel rays (rectilinear component) which are in the same direction as the direction of the incident light are combined with the reference light by a half-mirror HM. The reference light, that is, the light reflected from the beam splitter BS, is passed through a frequency shifter AO, e.g., an ultrasonic light modulator, where the frequency is slightly changed, before the above-described combination of light. When the reference light is photoelectrically converted after being combined with the specimen light, a signal containing an AC signal of a frequency corresponding to a difference in frequency between the reference light and the specimen light is output from a detector 2. Since the size of the AC component of the signal obtained from the detector 2 is proportional to the amplitude of the specimen light, the AC component is separated from the output of the detector 2 to obtain from the size of the AC component relative transmission characteristics or absorption characteristics in accordance with the wavelength of the incident light. The direction of the scattered light that is combined with the reference light does not necessarily need to be the same as that of the light incident on the specimen 20. In the absorption spectrum measured in this way, the light intensity changes in general as the wavelength of the laser 10 is swept. Therefore, when a highly directional detecting system is employed, part of the illuminating light beam is taken out, that is, a half-mirror is inserted in between the laser 1 and the specimen S, for example, in the arrangement shown in FIG. 3, to detect the intensity of the output laser light. When a heterodyne detecting system is employed, a light cut-off element is inserted in the rear of the speciment 20 in FIG. 4 to monitor the intensity of the laser output in the detector 2. It is also possible to instal a light intensity monitoring detector (not shown) in the rear of the half-mirror HM in FIG. 4.

FIG. 5 shows a reflection type apparatus for measuring spectral absorption characteristics in a specific direction of a specific specimen within a scattering medium, the apparatus being formed by modifying the apparatus employing the heterodyne light-receiving system 3 shown in FIG. 4. In this case, no specimen is disposed immediately behind the beam splitter BS, but the directional position of the half-mirror HM is changed and a scattering medium NZ (schematically shown) is disposed at a position where light that has been transmitted through the beam splitter BS and the half-mirror HM passes. In this arrangement, a specific specimen 21, which is schematically shown in the rear of the scattering medium NZ, reflects the forward scattered light in the reverse direction, and the reflected light is transmitted through the scattering medium NZ again in the reverse direction so that the reflected light that has been transmitted in this way is combined with the reference light by the half-mirror HM. This arrangement is particularly effective when the thickness of the scattering medium NZ is small and the proportion of the directly transmitted component to the other components is high.

Figure 2:
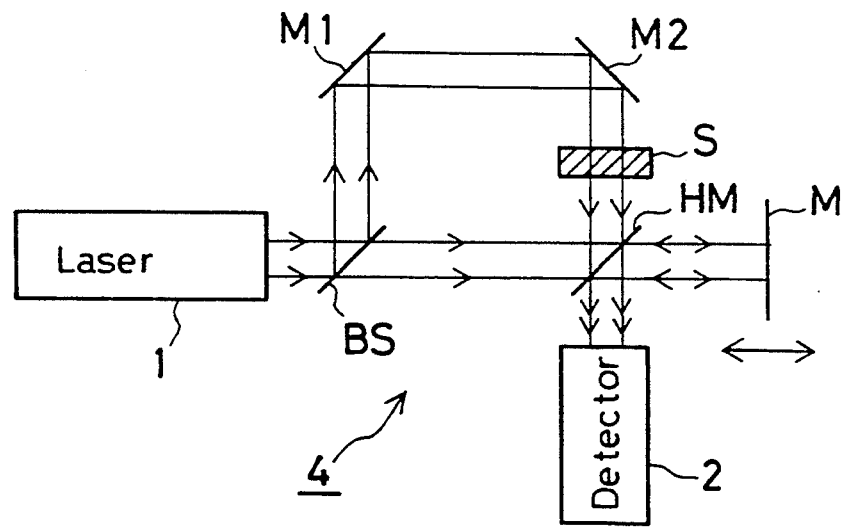
FIG. 2 is a view for explanation of the arrangement and operation of a Michelson light-receiving system as another highly directional detecting system.

FIG. 6 shows an apparatus to which the Michelson light-receiving system 4 shown in FIG. 2 is applied to measure spectral absorption characteristics of a transmitting specimen 20. In this arrangement, light that is emitted from a variable wavelength laser 10 is converted into a beam of parallel rays having a proper diameter through a beam converter 11 and is then split by a beam splitter BS into two light beams, that is, rectilinear light and reflected light. A transmitting specimen 20 is inserted in the path of the reflected light that is passed via mirrors M1 and M2, and the light that is transmitted through the specimen 20 while being scattered is combined with the reference light by a half-mirror HM. The reference light that is transmitted through the beam splitter BS is further transmitted through the half-mirror HM to strike upon a moving mirror M that is moved as shown by the double-head arrow in the figure. The reference light that is reflected from the mirror M in the reverse direction is combined with the specimen light by the half-mirror HM, and the resulting composite light is photoelectrically converted in a detector 2, from which is obtained a signal having an interference signal superposed thereon, the frequency of the interference signal corresponding to the speed of the moving mirror M. Since the intensity of the AC component of the signal output from the detector 2 is proportional to the intensity of the light scattered in the transmitting specimen 20, spectral absorption characteristics can be obtained from the intensity of the AC component by sweeping the wavelength of the variable wavelength laser 10.

FIG. 7 shows an arrangement employing the Michelson light-receiving system 4, which is adapted for reflecting specimens. The figure schematically shows a specific spectral reflecting specimen 21 in a scattering medium NZ. More specifically, the scattering medium NZ is disposed at a position where light reflected from a beam splitter BS passes. The specimen 21, which reflects the forward scattered light in the reverse direction, is schematically shown in the rear of the scattering medium NZ. The scattered light is transmitted through the scattering medium NZ again in the reverse direction and is then combined with the reference light reflected from the moving mirror M by the beam splitter BS. This arrangement is effective when the thickness of the scattering medium NZ is small and the proportion of the directly transmitted component to the other components is high, as in the case of the arrangement shown in FIG. 5.

Figure 9:
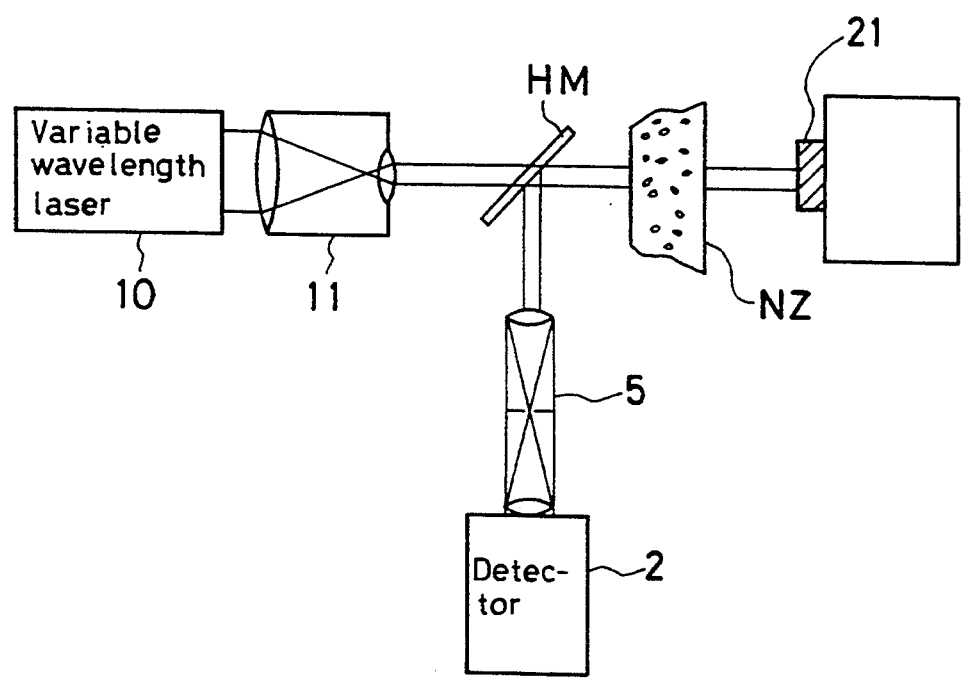

FIGS. 8 and 9 show apparatuses employing the typical highly directional optical system 5 shown in FIG. 3 to measure spectral absorption characteristics in a specific direction of a scattering component in transmitting and reflecting specimens 20 and NZ, thereby extracting only a scattering component in a specific direction. The apparatus shown in FIG. 8 is arranged for transmitting specimens, and the apparatus shown in FIG. 9 for reflecting specimens. Light from a variable wavelength laser 10 is converted into a beam of parallel rays with a proper diameter through a beam converter 11. In the arrangement shown in FIG. 8, the beam of light strikes directly upon a transmitting specimen 20 and is forwardly transmitted therethrough while being subjected to multiple scattering and absorption. In the arrangement shown in FIG. 9, the beam of light strikes upon a scattering medium NZ (schematically shown) via a half-mirror HM and is reflected from a specimen 21 in accordance with the reflecting spectral characteristics thereof. In the case of FIG. 8, only a component scattered in a specific direction is extracted by a highly directional optical system 5, and the intensity of the extracted scattering component is detected by a detector 2. Accordingly, in the case of FIG. 8, the oscillation wavelength of the variable wavelength laser 10 is swept and the reflected light from a half-mirror (not shown) disposed in between the beam converter 11 and the specimen 20 is detected to monitor the laser output, thereby obtaining transmission integral extinction. In the case of FIG. 9, the laser light that is reflected from the half-mirror HM is detected (no detector being shown) to monitor the laser output, thereby obtaining transmission integral extinction. It should be noted that in FIG. 9, the specimen 21, which reflects the forward scattered light in the reverse direction, is schematically shown in the rear of the scattering medium NZ shown schematically, in the same way as in the case of FIGS. 5 and 7. More specifically, the scattered light is transmitted through again in the reverse direction and then reflected from the half-mirror HM in a direction different from the direction of the incident light, thereby extracting only a component scattered in a specific direction by the highly directional optical system 5. The rest of the arrangement is the same as in the case of the apparatuses shown in FIGS. 4 to 7.

Figure 10:
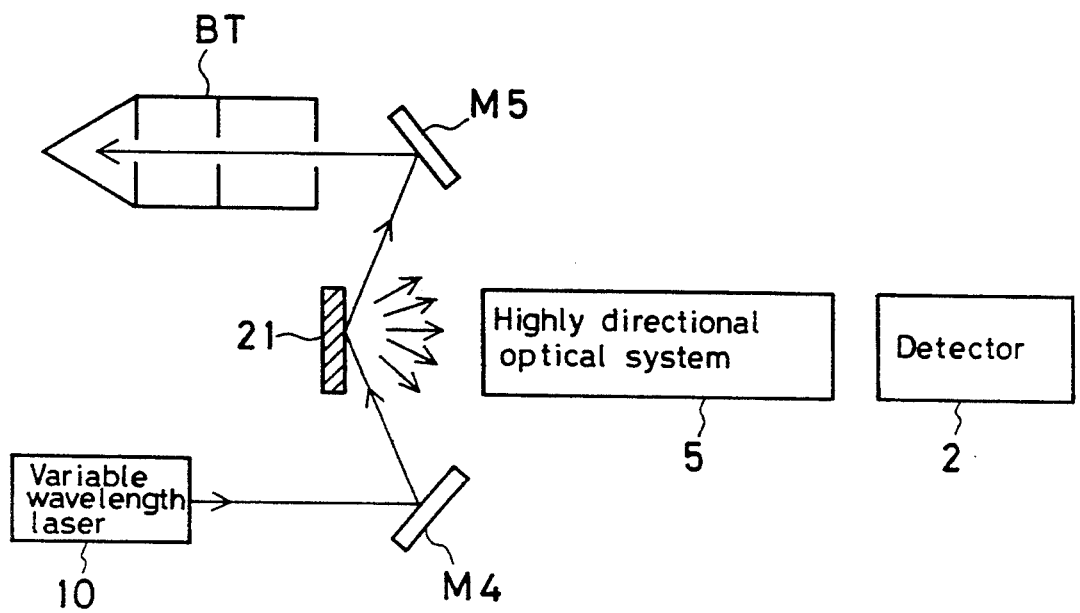
FIGS. 10 and 11 show the arrangements of embodiments of the spectral absorption measuring apparatus according to the present invention, which are applied to a reflecting specimen.
Figure 11:
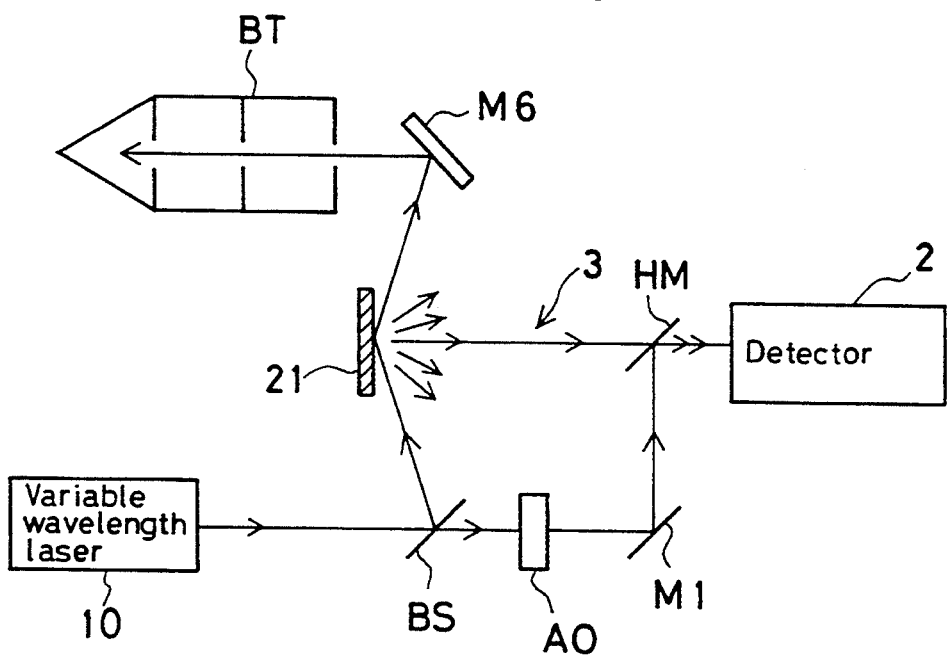

The foregoing apparatuses are arranged to measure spectral absorption characteristics of a transmitting or reflecting specimen, and in the case of a reflecting specimen which reflects light strongly at the surface thereof, these arrangements can be readily altered for this purpose. In the case of a reflecting specimen, however, when the intensity of the regular reflection component of the incident light is extremely high, the regular reflection component generally contains substantially no information about absorption characteristics in the vicinity of the surface of the reflecting specimen, and it is therefore necessary to remove the regular reflection component. FIGS. 10 and 11 exemplarily show apparatuses which are arranged to remove the regular reflection component. The apparatus shown in FIG. 10 is designed to extract a component scattered in a specific direction from a position in the vicinity of the surface of a reflecting specimen 21 by use of a highly directional optical system 5 as a highly directional optical system to thereby measure spectral absorption characteristics. In this apparatus, monochromatic light from a variable wavelength laser 10 is made incident on the surface of the reflecting specimen 21 through a mirror M4 at a certain angle with respect to the normal to the specimen surface, so that the regular reflection component of the incident light is removed by a beam trap BT through a mirror M5. The apparatus shown in FIG. 11 is designed to extract a component scattered in a specific direction from a position in the vicinity of the surface of a reflecting specimen 21 by use of a heterodyne light-receiving system 3 as a highly directional detecting system to thereby measure spectral absorption characteristics. In this apparatus also, a regular reflection component reflected from the surface of the specimen 21 is removed through a beam trap BT by an arrangement similar to that shown in FIG. 10.

Figure 12:
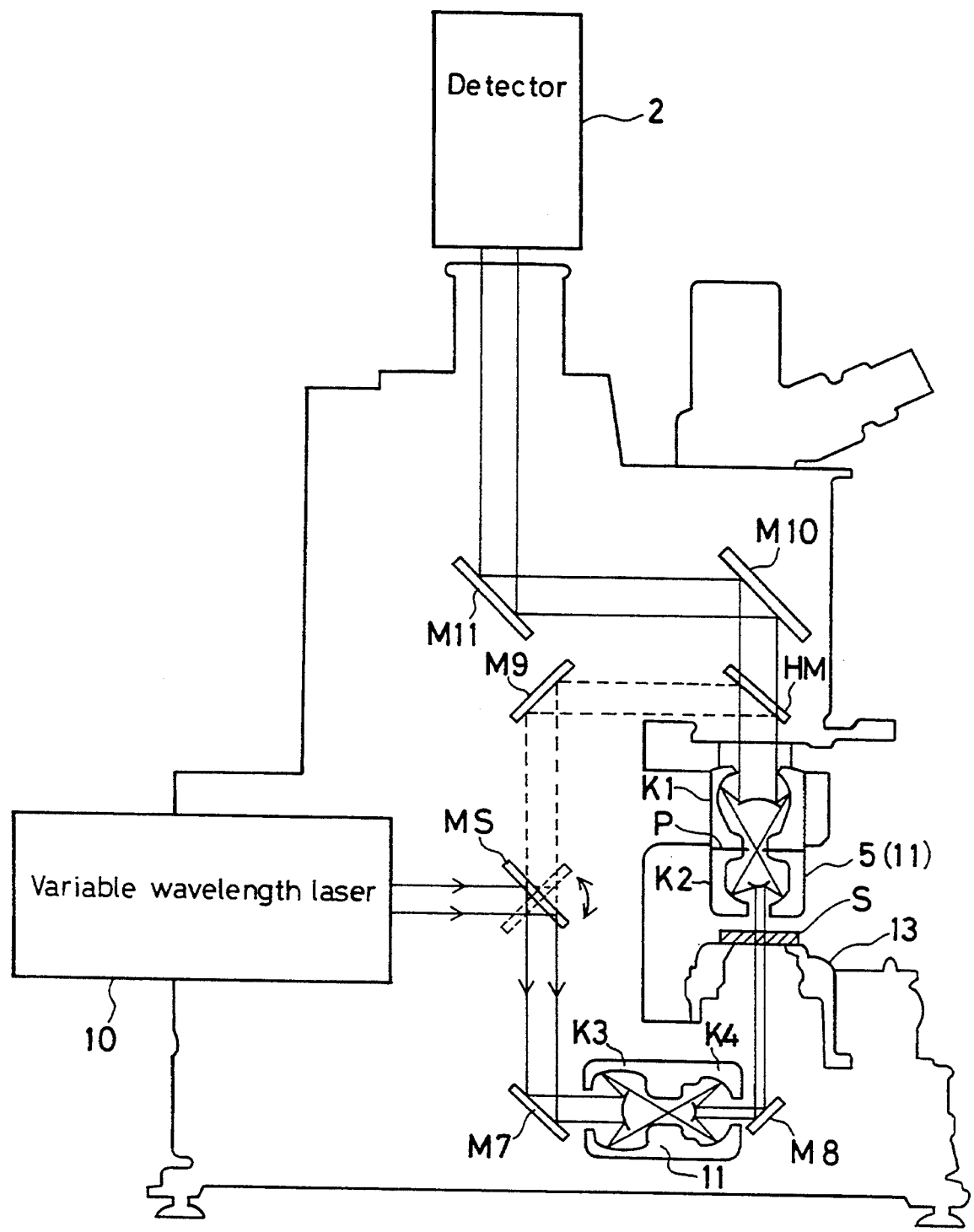
FIGS. 12 to 14 show specific examples of apparatus for measuring spectral absorption characteristics in a microsize region of a specimen.

Next, some specific examples of apparatus for measuring spectral absorption characteristics in a microsize region of a specimen will be briefly explained. FIG. 12 schematically shows the arrangement of an apparatus which is capable of measuring either transmission or reflection spectral absorption characteristics of a specimen S that is placed on a specimen table 13. In this apparatus, the course of monochromatic light from a variable wavelength laser 10 is changed over from one to the other of two optical paths, that is, a transmission optical path shown by the solid lines and a reflection optical path shown by the chain lines, by a switching mirror MS. When the solid-line optical path is selected, the light is passed via a mirror M7 and then converted into a beam of parallel rays with a predetermined diameter by a beam converter 11 comprising Cassegrain reflection optical systems K3 and K4, which are disposed confocally. Then, the beam of light enters the specimen S, and the light that is transmitted through the specimen S while being scattered in a specific direction is extracted by a highly directional optical system 5 comprising Cassegrain reflection optical systems K1 and K2, which are disposed confocally, and a pinhole P that is disposed at the confocal point. The scattered light thus extracted is then applied to a detector 2 via mirrors M10 and M11. Thus, spectral absorption characteristics of the transmission component of the specimen S can be obtained by sweeping the wavelength of the variable wavelength laser 10. If the switching mirror MS is changed over to the reflection optical path shown by the chain lines, the monochromatic light from the variable wavelength laser 10 is passed via a mirror M9 and reflected downwardly from a half-mirror HM. The reflected light then enters the specimen S after the beam diameter has been reduced through the highly directional optical system 5 that functions as a beam converter 11 in this case. Only the light that is scattered completely backwardly from the specimen S is extracted by the highly directional optical system 5, and the extracted light is then applied to the detector 2 via the half-mirror HM and the mirrors M10 and M11. Thus, spectral absorption characteristics of the reflection component of the specimen S can be obtained by sweeping the wavelength of the variable wavelength laser 10. When a backward scattering component of the specimen S other than the regular reflection component is to be extracted, light should be made incident on the specimen S that is tilted properly.

Figure 13:
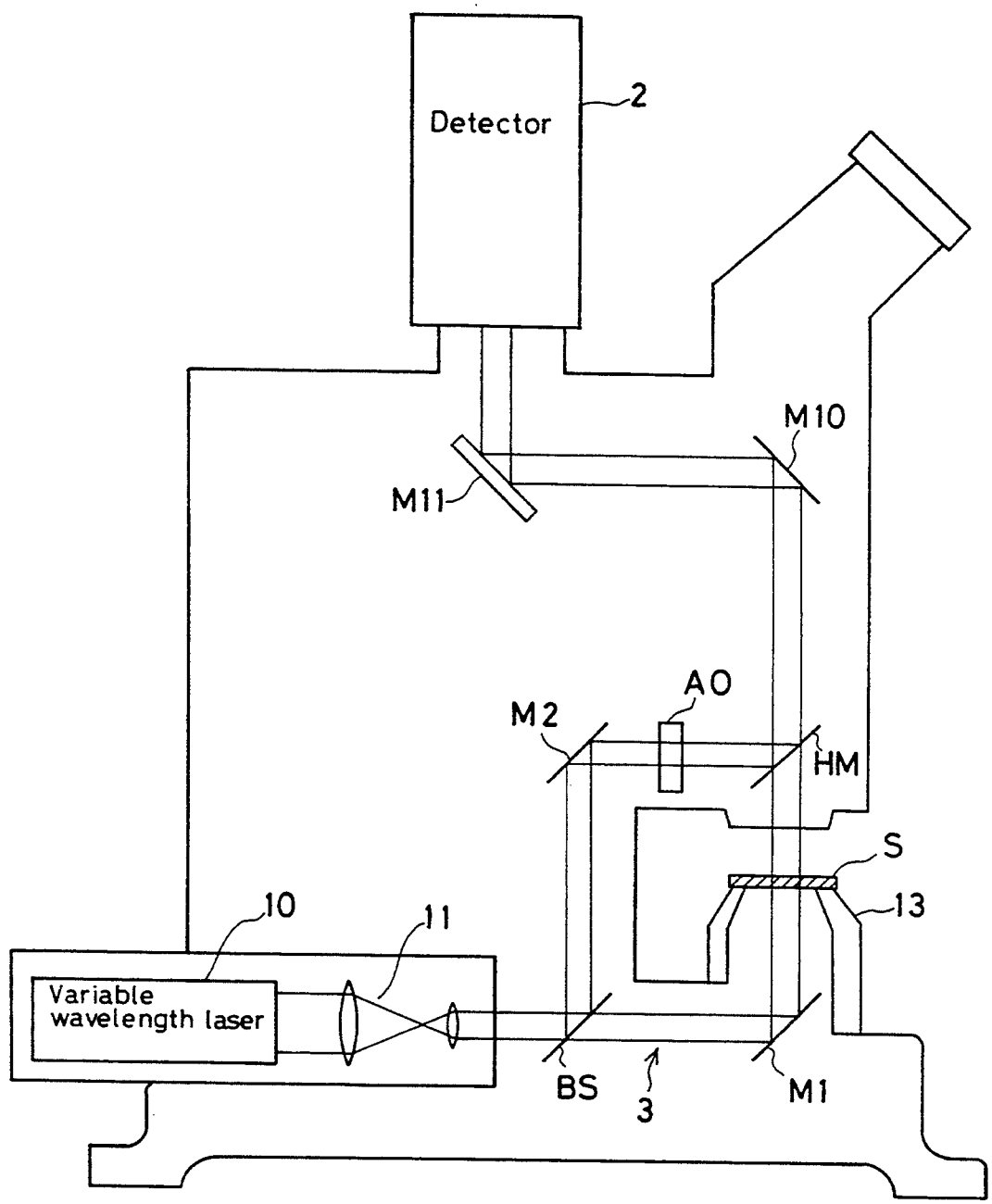
Figure 14:
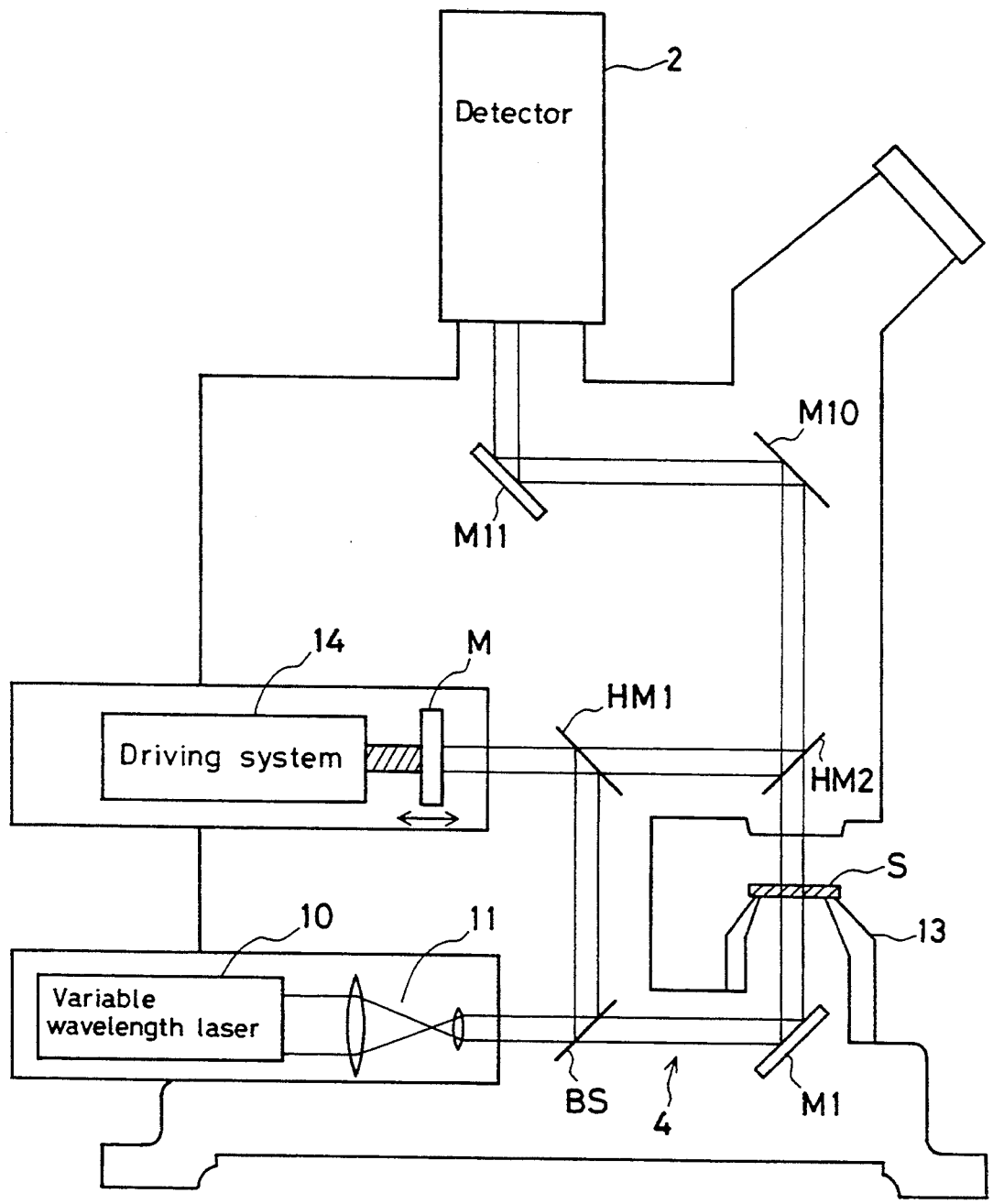

FIG. 13 shows an apparatus that employs the heterodyne light-receiving system 3 shown in FIG. 4, and FIG. 14 shows an apparatus that employs the Michelson light-receiving system 4 shown in FIG. 6. Since these apparatuses are modifications made simply by arranging the corresponding apparatuses shown in FIGS. 4 and 6 into a vertical form, no special explanation will be needed. It should be noted that in FIG. 14 a driving system 14 is provided to move a moving mirror M along an optical axis.

The following is a description of embodiments of the method of and apparatus for measuring a microscopic absorption distribution in an opaque specimen according to the present invention.

Figure 1:
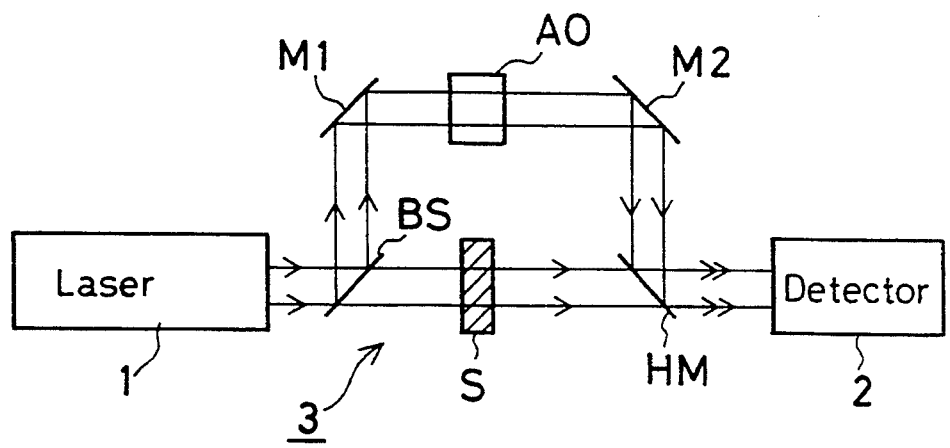
FIG. 1 is a view for explanation of the arrangement and operation of a heterodyne light-receiving system as one highly directional detecting system which is utilized in the present invention.

The relationship between the specimen S and the beam of parallel rays in the highly directional optical systems 3, 4 and 5, as shown in FIGS. 1 to 3, is changed to that in high-resolution detecting systems 30, 40 and 50 arranged as shown in FIGS. 15A to 17, thereby applying incident light to a vary small point region that corresponds to a 0-order diffraction component of a Fraunhofer diffration image formed by a lens, and thus making it possible to detect scattered light from only the very small point. More specifically, a condenser lens L1 with a relatively large numerical aperture (NA) is interposed at the light entrance side of the specimen S such that the back focal point of the lens L1 is coincident with a measuring point on the specimen S, and an objective lens L2 with a relatively large numerical aperture (NA) is disposed such that the front focal point of the lens L2 is coincident with the back focal point of the condenser lens L1. With this arrangement, light from a laser 1 is applied to a very small point on the specimen S through the condenser lens L1, and light emerging from the very small point is converted through the objective lens L2 into parallel rays traveling in a predetermined direction. Thus, only the light traveling in this direction is detected by a detector 2 on the principle of the highly directional detecting system 3, 4 or 5. In this way, it is possible to detect scattered light only from a very small region corresponding to a 0-order diffraction component of a Fraunhofer diffraction image of the specimen S formed by a lens. Accordingly, employment of the above-described high-resolution detecting system 30, 40 or 50 makes it possible to avoid mixing of unnecessary scattered light from the surroundings including the front and rear of the measuring point and also enables absorption characteristics of the specimen S to be measured with extremely high resolution.

Figure 15A:
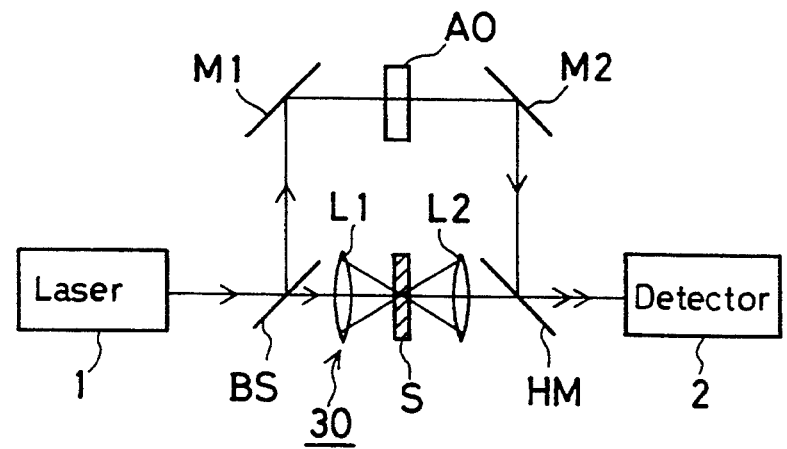
FIG. 15A is a view for explanation of the arrangement and operation of a high-resolution detecting system employing a heterodyne light-receiving system, which is employed in the method of and apparatus for measuring a microscopic absorption distribution in an opaque specimen according to the present invention.
Figure 15B:
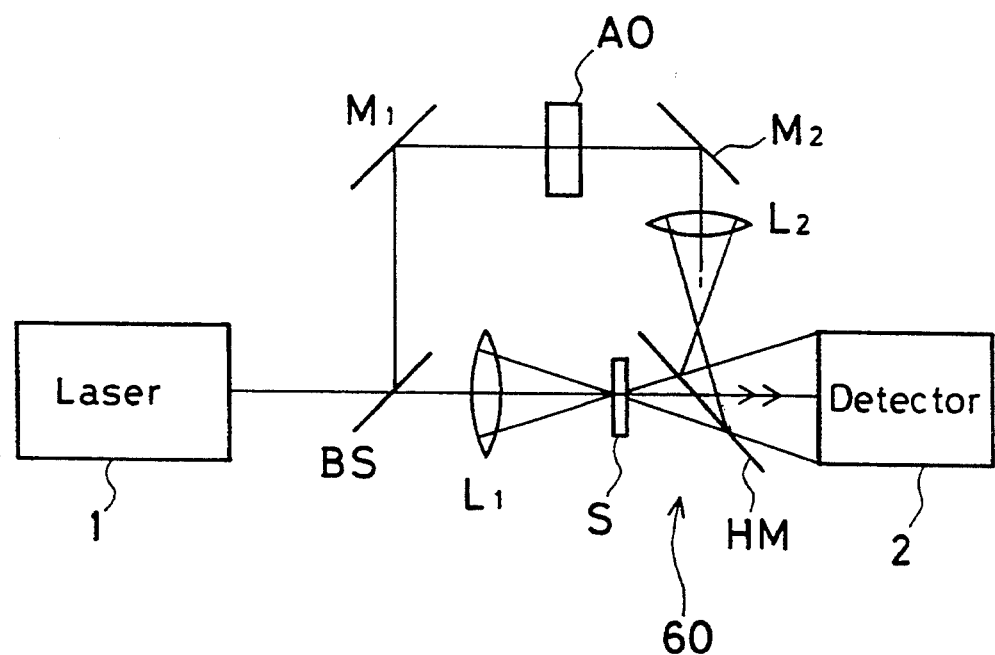
FIG. 15B shows a modification of the high-resolution detecting system shown in FIG. 15A.

FIG. 15B shows a modification of the apparatus shown in FIG. 15A. In FIG. 15A, light is applied to a very small point on the specimen S through the condenser lens L1, and the light emerging from this point is converted through the objective lens L2 into parallel rays (substantially plane wave) traveling in a predetermind direction before heterodyne reception. In FIG. 15B, however, the objective lens L2 is disposed in the optical path of the light beam emerging from the frequency shifter AO, and the condenser lens L1 and the objective lens L2 are arranged such that diverging spherical waves from the respective focal points of the condenser and objective lenses L1 and L2 coincide with each other. In this way, heterodyne detection is effected by the detector 2. The arrangement shown in FIG. 15B is as effective as the arrangement in FIG. 15A because a beat component that is obtained by heterodyne detection in which light is converted into a plane wave through a lens is equal to that obtained by heterodyne detection based on a spherical wave, that is, conditions required for wavefront matching in these two heterodyne detection methos are equal to each other.

In this case also, opaque specimens which may be first objects of the spectral absorption measurement in the present invention are not those which block incident light completely and do not transmit it forwardly, but sparse heterogeneous systems such as dilute suspensions, e.g., biological specimens, and also specimens such as dense translucent organic specimens, in which substantially no light is transmitted directly therethrough without being scattered, but light that is multiple-scattered forwardly by scattering fine particles in the specimen emerges therefrom. It is a matter of course that a specimen which transmits light directly therethrough can be employed as an object of the measurement. Second objects of the measurement in the present invention are those which cut off the incident light substantially completely and reflect as well as scatter it only backwardly, such as powder specimens. The former specimens will hereinafter be referred to as "transmitting specimens", and the latter specimens as "reflecting specimens".

Figure 18:
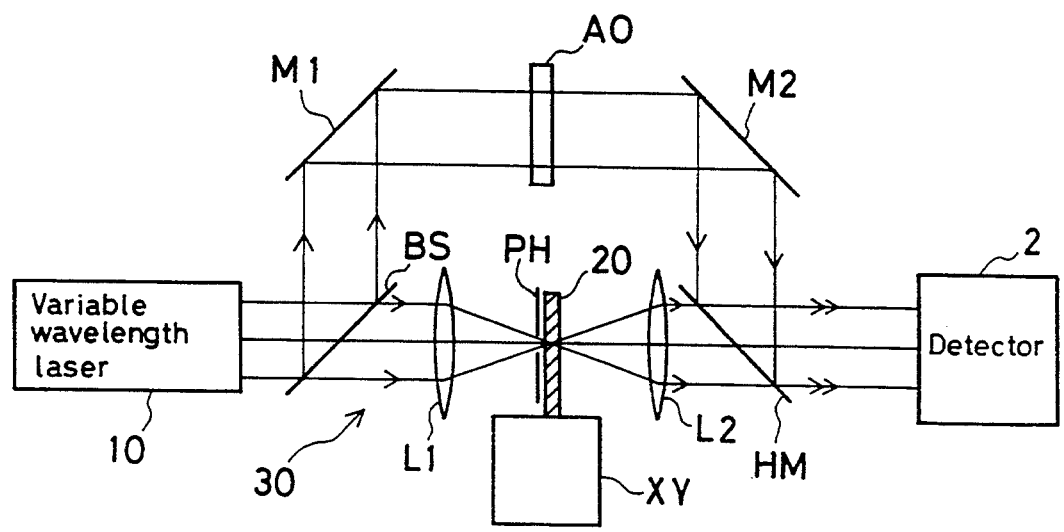
FIG. 18 shows the arrangement of one embodiment of the microscopic absorption distribution measuring apparatus employing a heterodyne light-receiving system according to the present invention, which is applied to a transmitting specimen.

FIG. 18 shows one embodiment of the apparatus for measuring a microscopic absorption distribution in an opaque specimen according to the present invention. This embodiment employs the high-resolution detecting system 30 comprising a heterodyne light-receiving system, shown in FIG. 15A, to measure a microscopic absorption distribution in a transmitting specimen 20. For such measurement, a variable wavelength laser 10 that can continuously emit monochromatic light sweepingly over a wide spectral range is employed as a monochromatic light source. A beam of light emitted from the laser 10 is divided through a beam splitter BS into two light beams, that is, rectilinear light and reflected light. The rectilinear light is condensed to a measuring point on the transmitting specimen 20 through a condenser lens L1, and the light transmitted through the specimen 20 while being scattered is converted into parallel rays through an objective lens L2 and then combined with reference light by a half-mirror HM. The reference light, that is, the light reflected from the beam splitter BS, is passed through a frequency shifter AO, e.g., an ultrasonic light modulator, where the frequency is slightly changed, before the above-described combination of light. When the reference light is photoelectrically converted after being combined with the specimen light, a signal containing an AC signal of a frequency corresponding to a difference in frequency between the reference light and the specimen light is output from a detector 2. Since the size of the AC component of the signal obtained from the detector 2 is proportional to the amplitude of the specimen light, the AC component is separated from the output of the detector 2 to obtain from the size of the AC component absorption characteristics at the measuring point. Since the intensity of the specimen light changes in accordance with the absorption characteristics at the measuring point of the specimen 20, by scanning the specimen 20 by the operation of an X-Y scanning device XY, it is possible to measure an absorption distribution over the scanned surface of the specimen 20. It is also possible to measure a spectral absorption distribution in the specimen 20 by measuring absorption at each measuring point while sweeping the wavelength of the laser 10. In order to make the measuring resolution smaller than the size of the 0-order diffraction pattern of the Fraunhofer diffraction pattern formed by the lenses L1 and L2, the illuminated region may be restricted by disposing a pinhole plate PH which is smaller than the size of the 0-order pattern in extremely close proximity to the measuring point (the focal point of the lens L1). In this case, the resolution improves, but the quantity of transmitted light decreases, disadvantageously. It should be noted that such a pinhole plate PH may be similarly disposed in embodiments described below.

Figure 19:
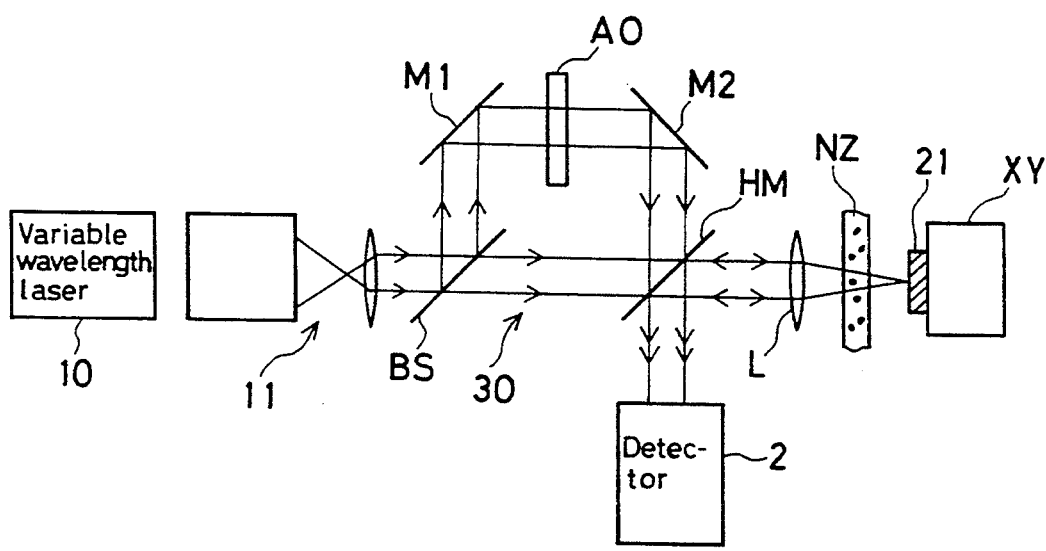
FIG. 19 shows the arrangement of one embodiment of the microscopic absorption distribution measuring apparatus, which is formed by modifying the apparatus shown in FIG. 18 so that it is applicable to a reflecting specimen.

FIG. 19 shows an apparatus formed by modifying the apparatus employing the high-resolution detecting system 30, shown in FIG. 18, so as to measure a reflecting specimen 21 that causes scattering. In this case, a beam converter 11 is disposed in front of the laser 10 in order to convert a beam of light emitted from the laser 10 into a beam of parallel rays with a proper diameter. This beam converter 11 is, however, not always needed. In this arrangement, the half-mirror HM shown in FIG. 18 is turned in the directional position, and a lens L that functions as both a condenser lens and an objective lens is disposed at a position where light from the laser 10 that is transmitted through the beam splitter BS and the half-mirror HM passes. The reflecting specimen 21 is disposed on the back focal plane of the lens L so that the reflected scattered light from the specimen 21 is combined with the reference light by the half-mirror HM. When a scattering medium NZ is schematically drawn as if it were present in front of the specimen 21, for example, as illustrated, the light scattered by the scattering medium NZ results in a DC component of the output from the detector 2. Thus, if the high-resolution detecting system 30 is employed, the scattered light is not detected as an AC component by the detector 2.

Figure 16:
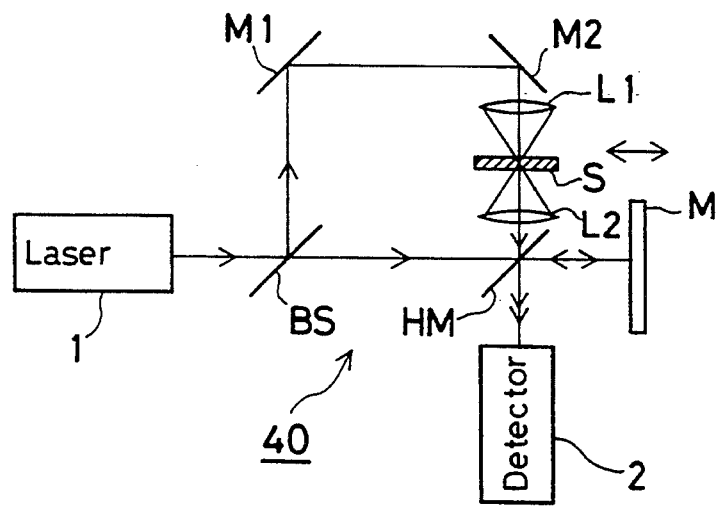
FIG. 16 is a view for explanation of the arrangement and operation of a high-resolution detecting system employing a Michelson light-receiving system, which is employed in the method of and apparatus for measuring a microscopic absorption distribution in an opaque specimen according to the present invention.
Figure 20:
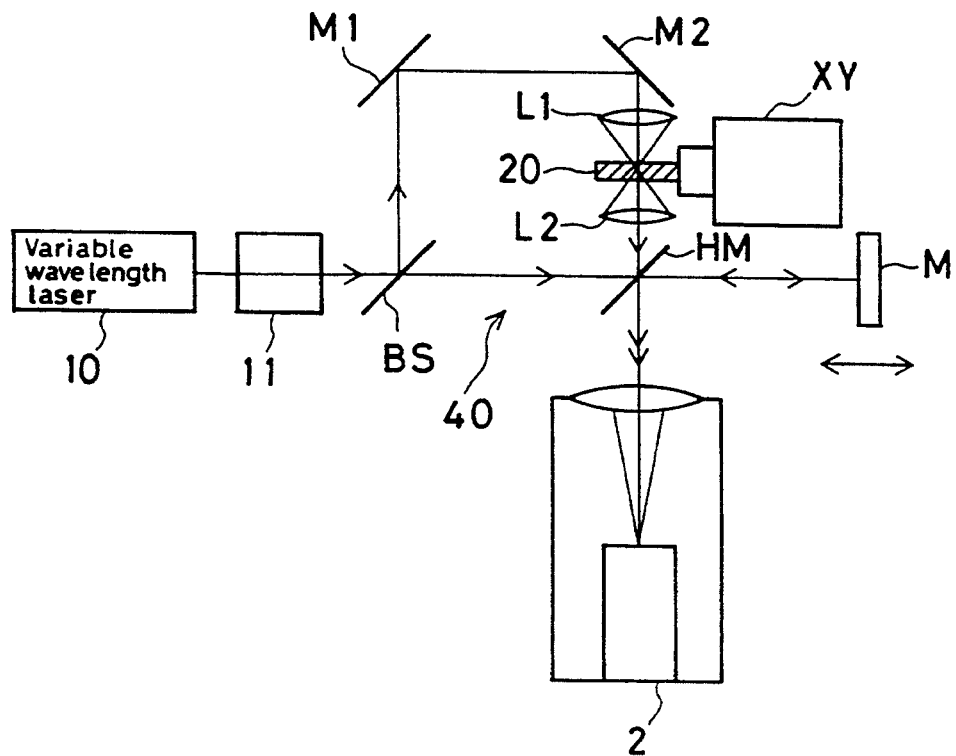
FIG. 20 shows the arrangement of one embodiment of the microscopic absorption distribution measuring apparatus employing a Michelson light-receiving system according to the present invention, which is applied to a transmitting specimen.

FIG. 20 shows an apparatus which employs the high-resolution detecting system 40 comprising a Michelson light-receiving system, shown in FIG. 16, to measure a microscopic absorption distribution in a transmitting specimen 20. In this apparatus, light that is emitted from a variable wavelength laser 10 is converted through a beam converter 11 into a beam of parallel rays with a proprer diameter and then divided through a beam splitter BS into two light beams, that is, rectilinear light, i.e., reference light, and reflected light. A condenser lens L1 and an objective lens L2 are disposed confocally in the path of the reflected light that is passed via mirrors M1 and M2, and a transmitting specimen 20 is inserted at the confocal position. The light that is transmitted through the specimen 20 while being scattered is combined with the reference light by a half-mirror HM. The reference light, which is light passing through the beam splitter BS, passes through the half-mirror HM to strike upon a moving mirror M that is moved as shown by the double-headed arrow in the figure. The reference light, which is reflected from the moving mirror M in the reverse direction, is combined with the specimen light by the half-mirror HM, and the resulting composite light is photoelectrically converted in a detector 2. The detector 2 outputs a signal upon which is superposed an interference signal the frequency of which corresponds to the speed of the moving mirror M. Since the intensity of the AC component of the output signal is proportional to the intensity of the scattered light from the transmitting specimen 20, an absorption distribution in the specimen 20 can be measured by obtaining the size of the AC component at each measuring point while scanning the specimen 20 by an XY scanning device XY. It is also possible to measure a spectral absorption distribution by obtaining an absorption distribution while sweeping the wavelength of the variable wavelength laser 10.

Figure 21:
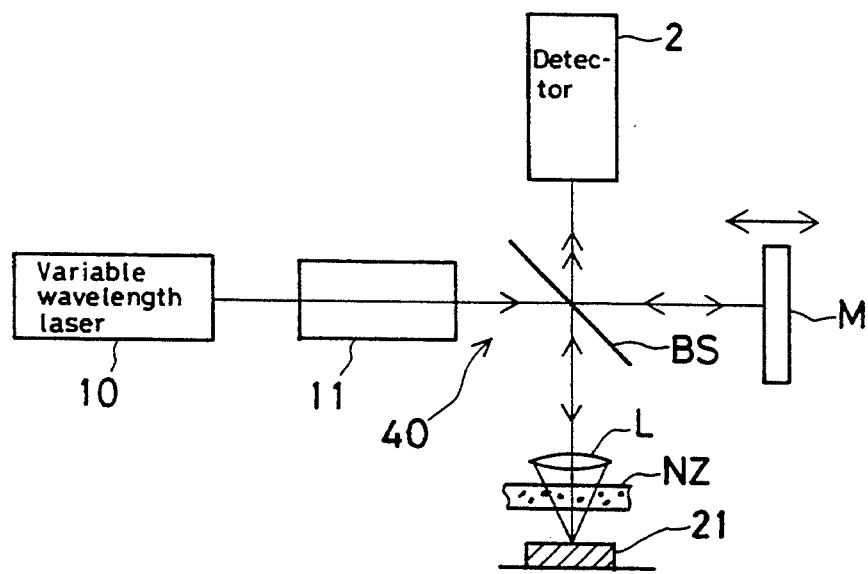
FIG. 21 shows the arrangement of one embodiment of the microscopic absorption distribution measuring apparatus, which is formed by modifying the apparatus shown in FIG. 20 so that it is applicable to a reflecting specimen.

FIG. 21 shows an apparatus formed by modifiying the high-resolution detecting system 40 utilizing a Michelson light-receiving system so as to obtain an absorption distribution in a reflecting specimen 21. In this case, a lens L that functions as a condenser lens and an objective lens is disposed at a position where light reflected from a beam splitter BS passes, and a reflecting specimen 21 is disposed on the back focal plane of the lens L, so that the reflected and scattered light from the specimen 21 is combined by the beam splitter BS with the reference light reflected from a moving mirror M.

Figure 17:
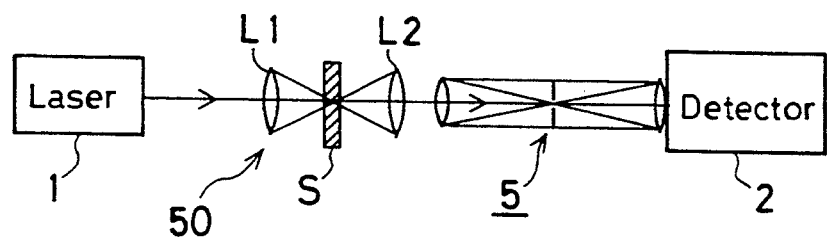
FIG. 17 is a view for explanation of the arrangement and operation of a high-resolution detecting system employing a highly directional optical system, which is employed in the method of and apparatus for measuring a microscopic absorption distribution in an opaque specimen according to the present invention.
Figure 22:
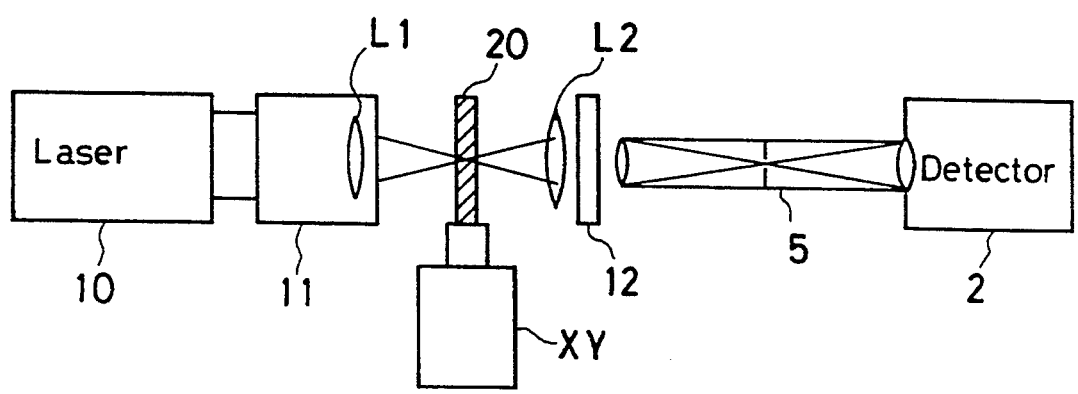
FIGS. 22 and 23 show the arrangements of embodiments of the microscopic absorption distribution measuring apparatus employing a highly directional optical system according to the present invention.
Figure 23:
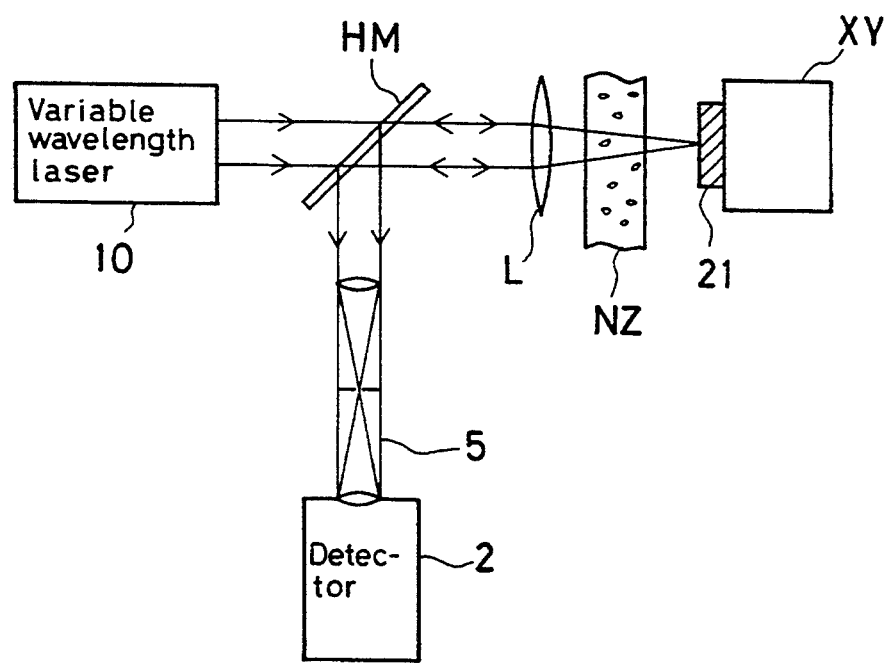

FIGS. 22 and 2 3 show apparatuses which employ high-resolution detecting system 50 employing the highly directional optical system 5, shown in FIG. 17, to measure an absorption distribution in a transmitting specimen 20 (FIG. 22) or a reflecting specimen 21 (FIG. 23). In the apparatus shown in FIG. 22, an excited light cut-off filter 12 that passes only fluorescent light produced at a measuring point on the specimen 20 is inserted in the rear of an objective lens L2 to measure a microscopic fluorescence distribution in the specimen 20. In the case of measurement of an absorption distribution, the excited light cut-off filter 12 is removed. In the measurement of a microscopic absorption distribution, light from a laser 10 is converted through a beam converter 11 into a beam of parallel rays with a proper diameter and is then condensed to a measuring point on the transmitting specimen 20 through a condenser lens L1. Light that is transmitted through the measuring point or scattered forwardly therefrom is converted into parallel rays through an objective lens L2 that is disposed such that its front focal point is coincident with the measuring point, and then separated in a highly directional optical system 5 from light that travels in the other directions. Then, the intensity of the specimen light is detected by a detector 2. Accordingly, an absorption distribution in the specimen 20 can be measured by obtaining the intensity of light from each measuring point while scanning the specimen 20 by an XY scanning device XY. In this case also, a spectral absorption distribution can be measured by obtaining an absorption distribution while sweeping the wavelength of the variable wavelength laser 10. However, in a case where the excited light cut-off filter 12 is inserted to measure a fluorescence distribution, the wavelength sweeping of the laser 10 is not conducted, or a fixed wavelength laser is employed in place of the variable wavelength laser 10. In the case of the apparatus for measuring an absorption distribution in the reflecting Specimen 21, shown in FIG. 23, a lens L that functions as both a condenser lens and an objective lens is disposed at a position where light transmitted through a half-mirror HM passes, and a reflecting specimen 21 is disposed on the back focal plane of the lens L. With this arrangement, the light reflected and scattered from the reflecting specimen 21 is converted into parallel rays through the lens L and then reflected by the half-mirror HM in a direction different from the direction of the incident light, thereby extracting only the light from the measuring point on the reflecting specimen 21 by a highly directional optical system 5. The rest of the arrangement is the same as that shown in FIG. 22.

Incidentally, the light intensity changes in general as the wavelength of the laser 10 is swept. Therefore, when a highly directional detecting system is employed, part of the illuminating light beam is taken out, that is, a half-mirror is inserted in between the laser 1 and the specimen S, for example, in the arrangement shown in FIG. 3, to detect the intensity of the output laser light. When a heterodyne detecting system is employed, a light cut-off element is inserted in the rear of the speciment 20 in FIG. 15A to monitor the intensity of the laser output in the detector 2. It is also possible to instal a light intensity monitoring detector (not shown) in the rear of the half-mirror HM in FIG. 15A. The light intensity detected in these ways is defined as the intensity of reference light, and the intensity of light transmitted through the specimen S or reflected in a specific direction is detected as the intensity of signal light by a highly directional detecting system or a heterodyne detecting system. With these values, a transmission integral extinction is determined to obtain an absorption spectrum of the specimen. This is a method that has already been employed in the conventional method of obtaining an absorption spectrum of an opaque specimen or in the method of obtaining absorbance of a specimen that causes no scattering.

Figure 24:
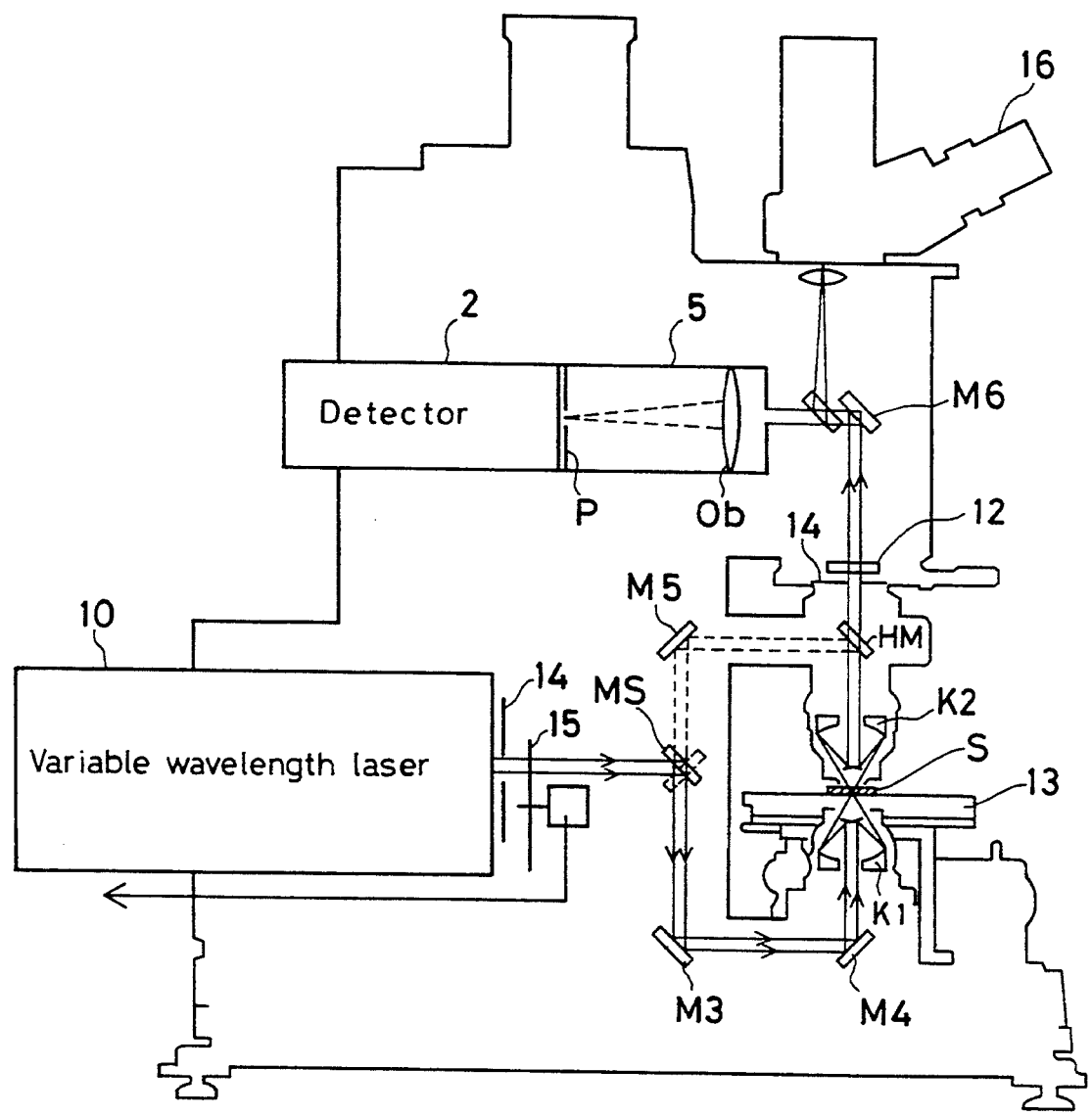
FIGS. 24 to 26 show specific examples of apparatus for measuring microscopic absorption distribution characteristics of a specimen according to the present invention.

Next, some specific examples of apparatus for measuring microscopic absorption distribution characteristics in a microsize region of a specimen will be briefly explained. FIG. 24 schematically shows the arrangement of an apparatus which is capable of measuring either transmission or reflection absorption characteristics of a specimen S that is placed on a specimen table 13 capable of being scanned in directions X and Y. In this apparatus, the course of monochromatic light from a variable wavelength laser 10 is changed over from one to the other of two optical paths, that is, a transmission optical path shown by the solid lines and a reflection optical path shown by the chain lines, by a switching mirror MS. When the solid-line optical path is selected, the light is passed via mirrors M3 and M4 and then condensed to a measuring point on a specimen S by a Cassegrain reflection optical system K1 that functions as a condenser lens L1. Light that is transmitted through the specimen S is converted into a beam of parallel rays by a Cassegrain reflection optical system K2 that functions as an objective lens and then passed via a mirror M6 to enter a highly directional optical system 5 comprising, for example, an objective lens Ob and a pinhole P which is disposed at the focal point thereof, shown in FIG. 29. Light from points other than the measuring point is removed by the highly directional optical system 5, and the intensity of light that represents absorption characteristics of the specimen S is detected by a detector 2. Accordingly, a transmission absorption distribution in the specimen S can be measured by obtaining the intensity of light from each measuring point while scanning the specimen S in the directions X and Y. If the switching mirror MS is changed over to the reflection optical path shown by the chain lines, the monochromatic light from the variable wavelength laser 10 is passed via a mirror M5 and reflected downwardly from a half-mirror HM. The reflected light is then condensed to a measuring point on the specimen S through the Cassegrain reflection optical system K2 that functions as both a condenser lens and an objective lens. Light that is scattered backwardly from the measuring point is converted into parallel rays through the Cassegrain reflection optical system K2 and passed via the mirror M6 to enter the highly directional optical system 5 where light from points other than the measuring point is removed. Then, the intenity of light that represents reflection absorption characteristics of the specimen S is detected by the detector 2. Thus, a reflection absorption distribution in the specimen S can be measured by obtaining the intensity of light from each measuring point while scanning the specimen S in the directions X and Y, in the same way as the above. It is possible to measure a microscopic fluorescence distribution by inserting an excited light cut-off filter 12 in the rear of the Cassegrain reflection optical system K2. Reference numeral 15 in the figure denotes a chopper which is provided to remove noise by modulating the laser light applied to the specimen S by a predetermined frequency and effecting synchronous detection. Reference numerals 14 and 16 denote an aperture and an eyepiece, respectively.

Figure 25:
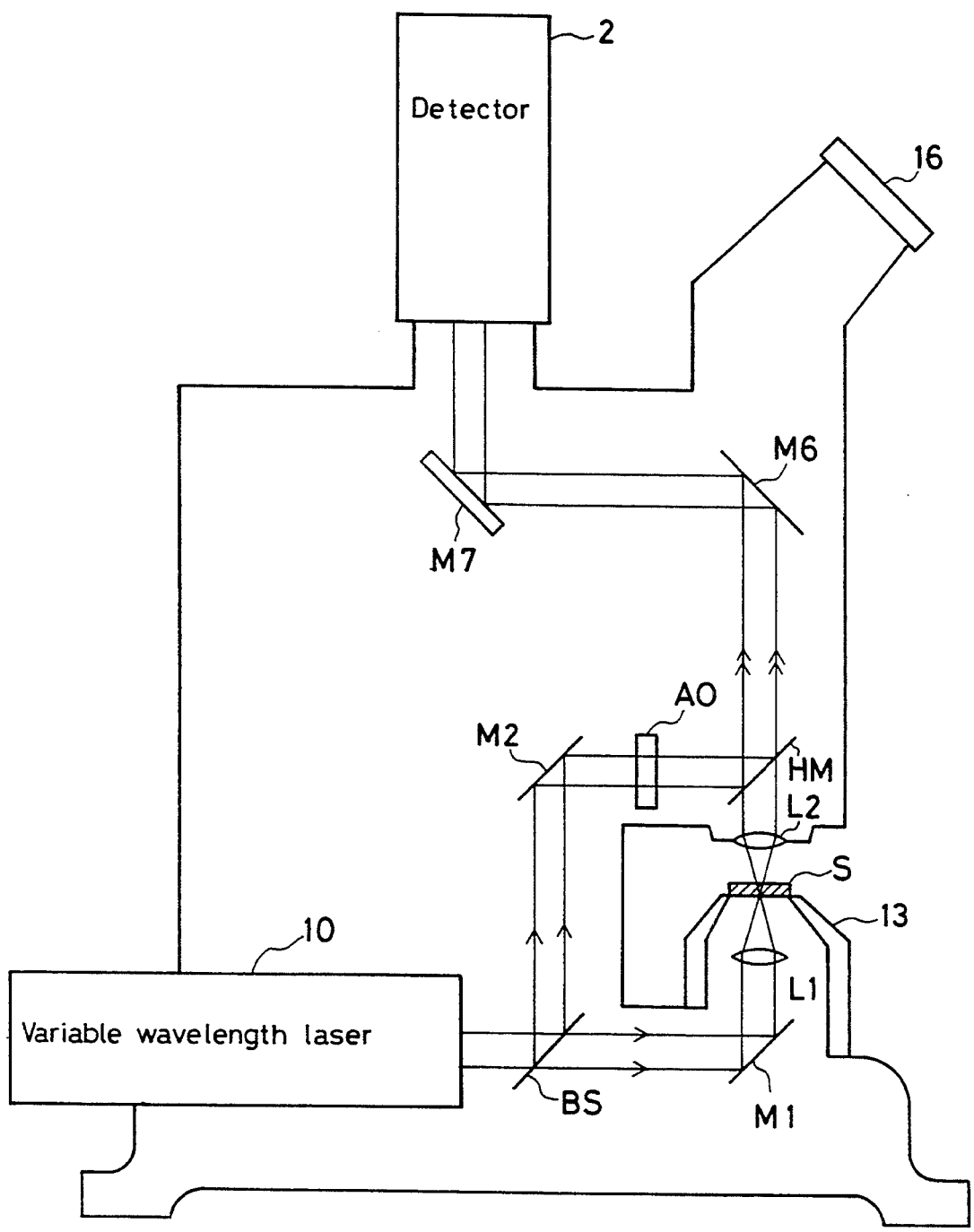
Figure 26:
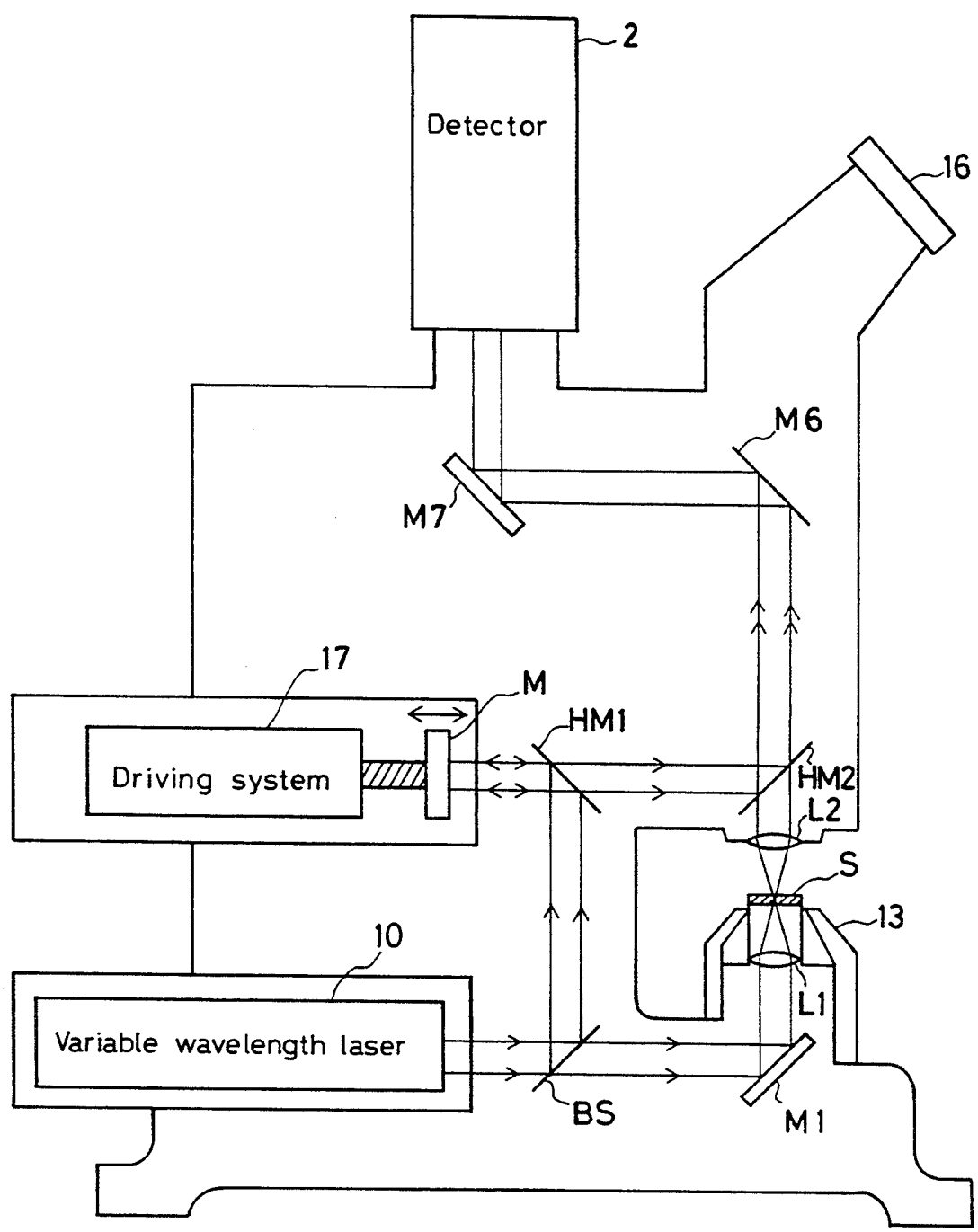
Figure 27:
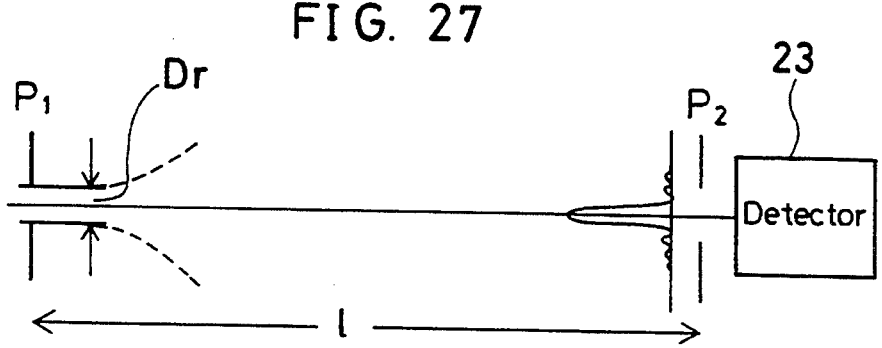
FIGS. 27 to 36 show the arrangements of highly directional optical systems proposed by the present inventor prior to this application.
Figure 28:
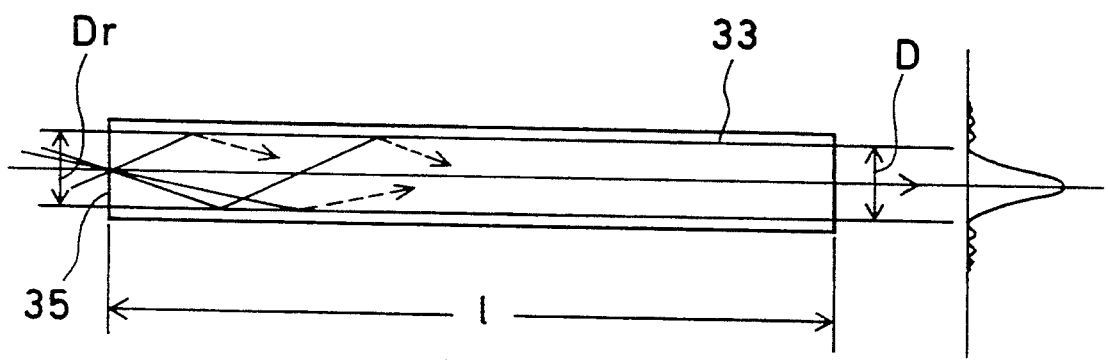
Figure 29:
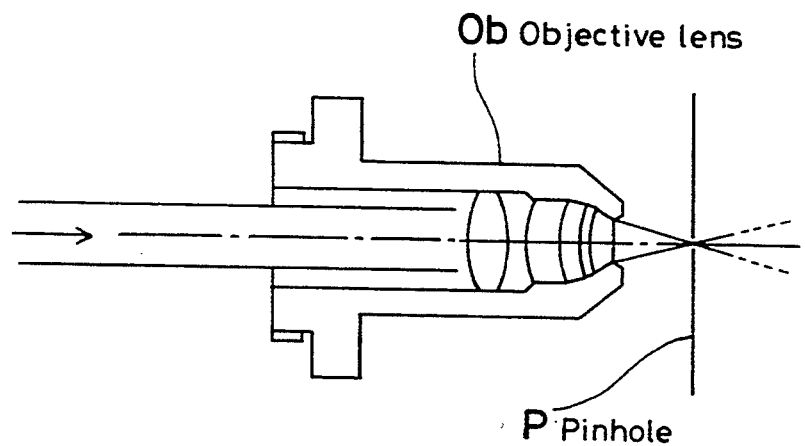
Figure 30:
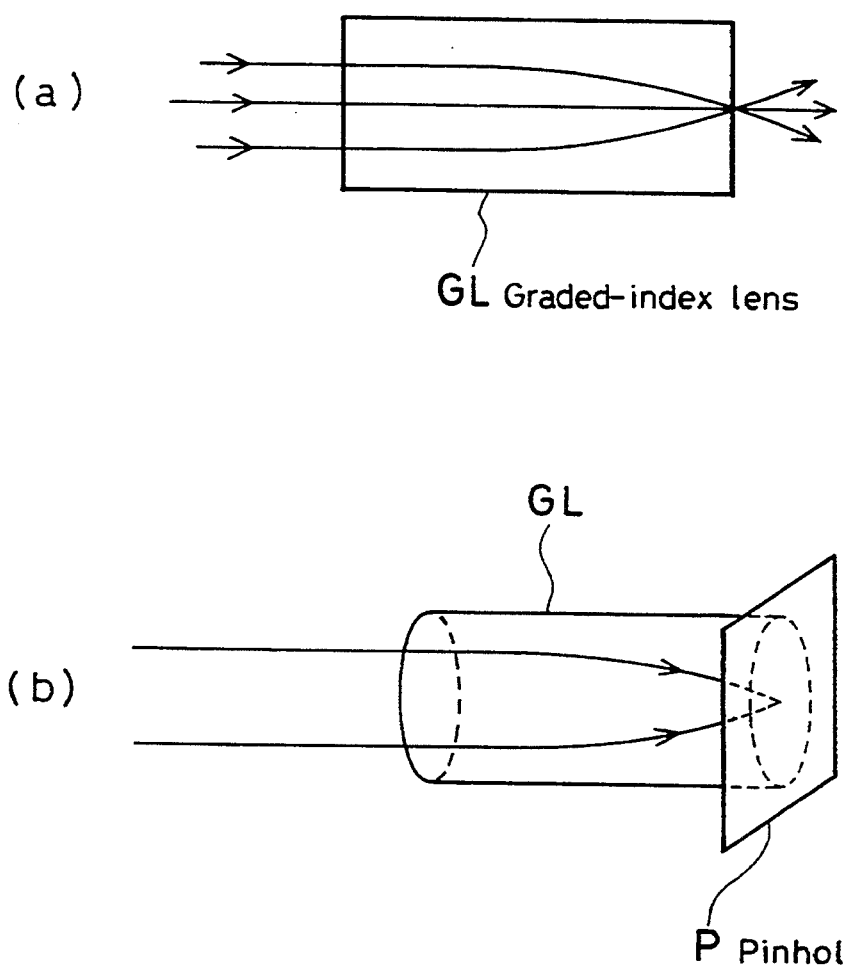
Figure 31:
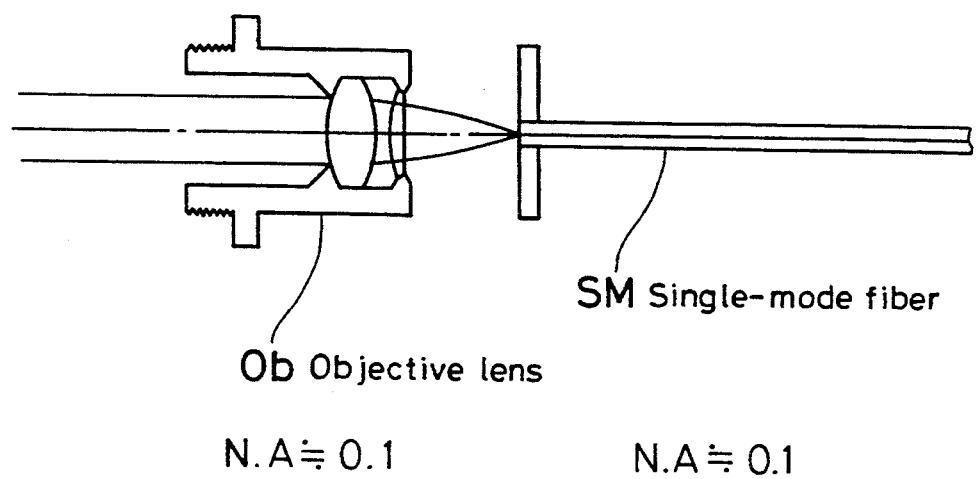
Figure 32:
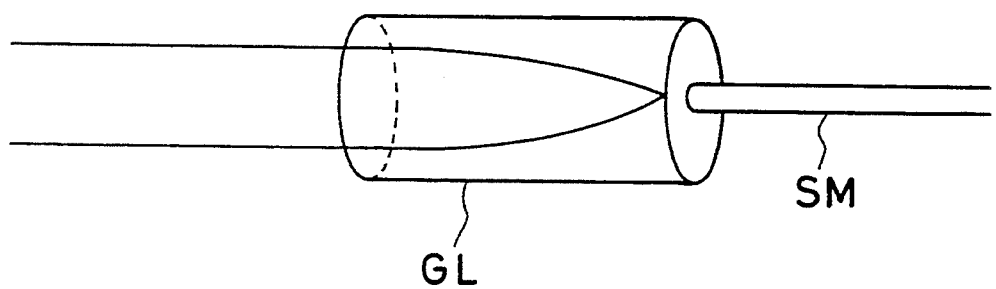
Figure 33:
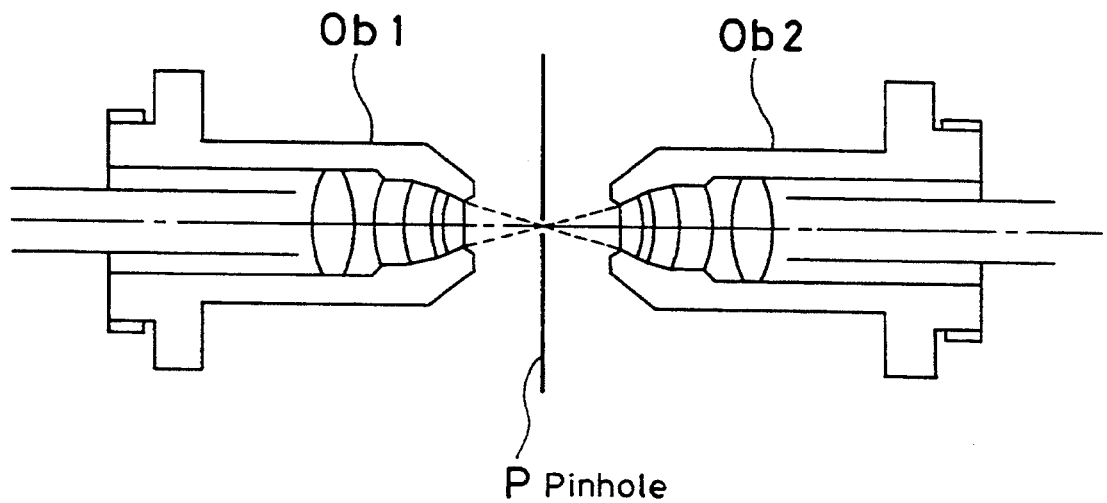
Figure 34:
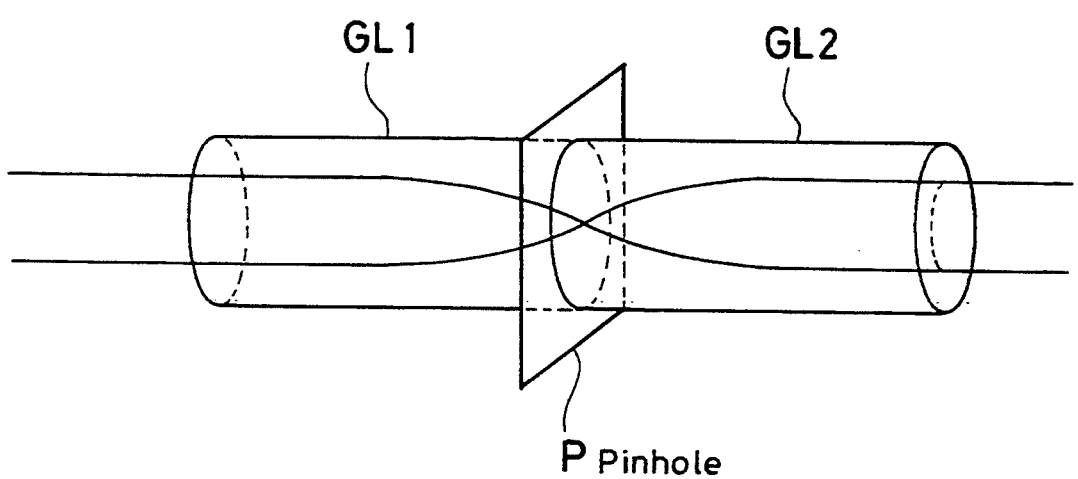
Figure 35:
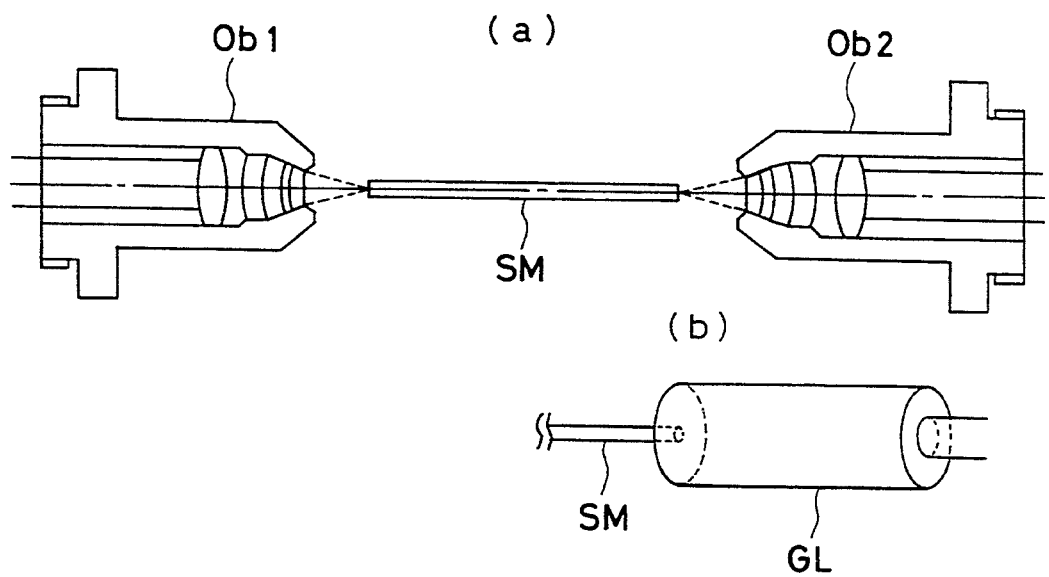
Figure 36:
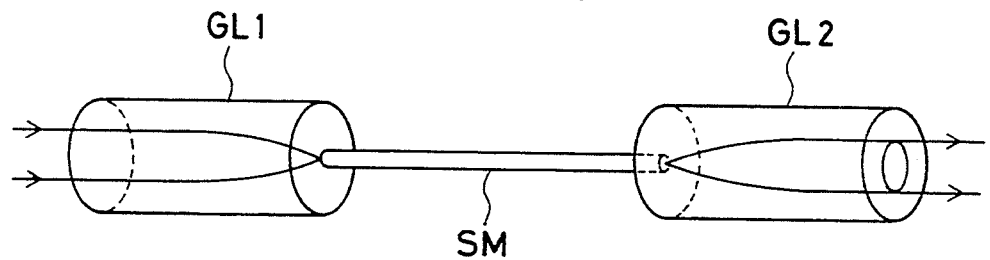
Figure 37:
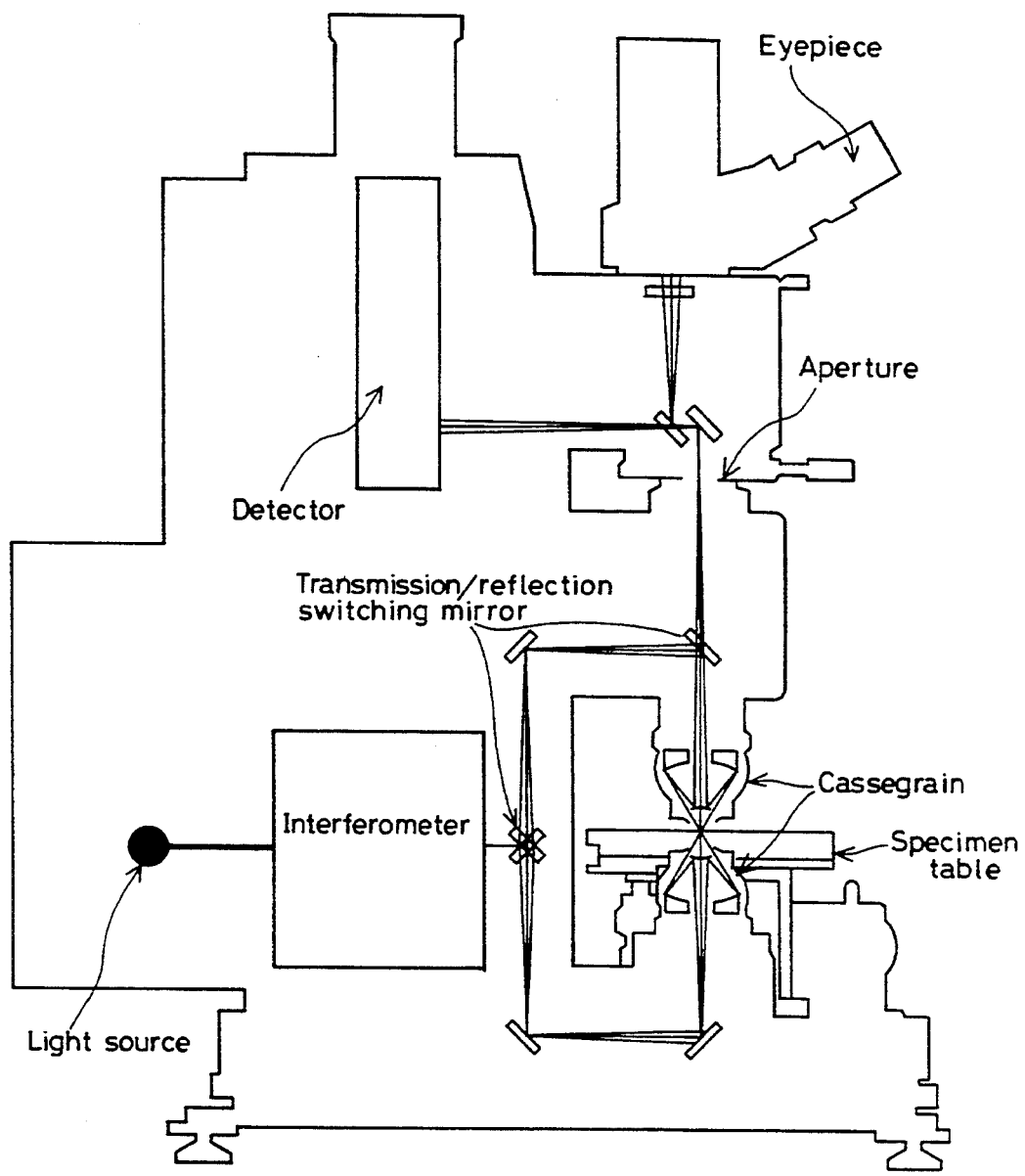
FIG. 37 shows the arrangement of a conventional apparatus for measuring microscopic absorption distribution, which employs a Fourier spectroscope.
Figure 38:
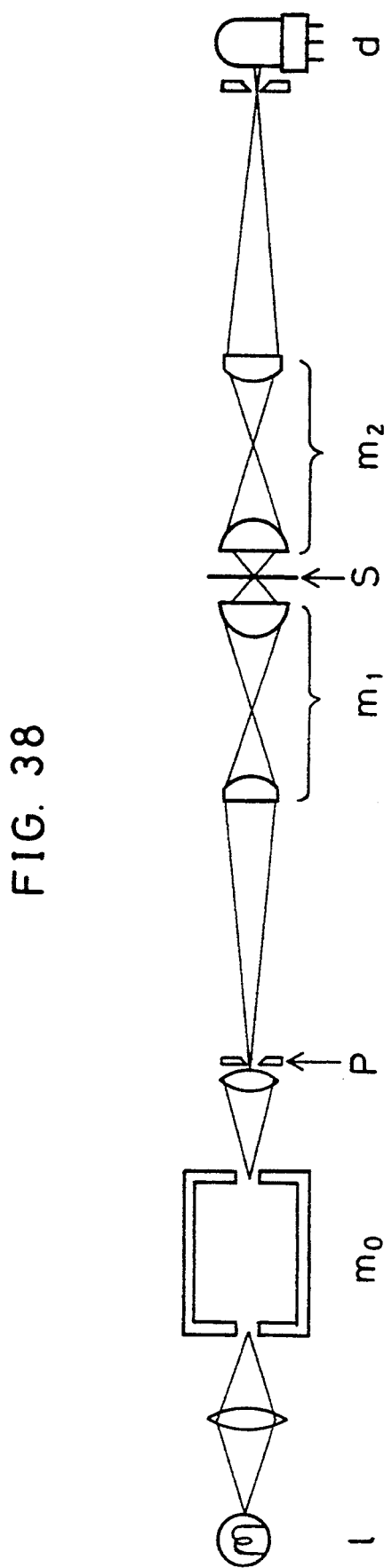
FIG. 38 shows the arrangement of a conventional apparatus for measuring microscopic absorption distribution in a very small specimen, which employs a diffraction grating spectroscope.

FIG. 25 shows an apparatus that employs the high-resolution detecting system 30 comprising a heterodyne light-receiving system, shown in FIG. 15A, and FIG. 26 shows an apparatus that employs the high-resolution detecting system 40 comprising a Michelson light-receiving system, shown in FIG. 16. Since these apparatuses are modifications made simply by arranging the corresponding apparatuses shown in FIGS. 15A and 16 into a vertical form, no special explanation will be needed. It should be noted that in FIG. 26 a driving system 17 is provided to move a moving mirror M along an optical axis.

Although in the foregoing embodiments the variable wavelength laser 10 is assumed to be oscillating continuously, it should be noted that a variable wavelength pulsed laser may also be employed. It is particularly preferable to employ a variable wavelength pulsed laser in the case of a specimen whose properties change rapidly when laser light is applied thereto continuously. Although no special explanation has been made on the detector 2, any known detecting means may be employed. As another example of the method of processing a detected signal, it is possible to modulate the intensity of the incident light by means of a chopper or the like and detect a signal by the phase lock technique. In this case, since the time constant in the detection of infrared is long, the synchronous modulation frequency needs to be lowered. It is also possible to employ synchronous signal integration detecting methods, e.g., photon counting method (visible light), charge storing method (infrared light), etc., and heterodyne beat signal detecting method, and so forth. As to the frequency shifter, it is possible to employ not only those which employ ultrasonic light diffraction, e.g., an ultrasonic modulator, but also a combination of wave plates, a diffraction grating, or a frequency shifter that utilizes the electrooptic effect of a crystal. The reflecting mirror in the Michelson interferometer may be either moved at a constant speed or oscillated by saw-tooth wave. For heterodyne reception, it is also possible to employ two lasers, in addition to the above-described arrangement in which light from a single laser as a monochromatic light source is divided into two beams of light to form locally oscillated light.

As has been described above, in the method of and apparatus for measuring spectral absorption in an opaque specimen according to one aspect of the present invention, a scattering specimen is illuminated with highly directional light of variable wavelength from a specific direction, thereby removing scattered rays as much as possible, and thus detecting the intensity of only parallel rays of a component transmitted or reflected in a specific direction (i.e., rectilinear component rays) by use of a highly directional detecting system, for example, a heterodyne light-receiving system, Michelson light-receiving system, highly directional optical system, etc. It is therefore possible to measure spectral absorption characteristics of a scattering specimen with high accuracy without picking up scattered light in other undesired directions nor other noise light. In addition, the measurement of the control is exceedingly simplified in comparison to the conventional method and thus the measurement is extremely facilitated. Thus, the method and apparatus of the present invention are suitable for measuring spectral absorption of a component transmitted or reflected in a specific direction in not only sparse heterogeneous systems having spatial resolving power, for example, suspensions, organic tissues, etc., but also dense transparent objects that cause scattering to a substantial degree.

In the method of and apparatus for measuring a microscopic absorption distribution in an opaque specimen according to another aspect of the present invention, a very small measuring point on a specimen is illuminated with a condensed light of high directivity, and light that diverges from the measuring point is converted into parallel rays, or left as it is in the form of a spherical wave, and then detected by use of a highly directional detecting system, for example, a heterodyne light-receiving system, Michelson light-receiving system, highly directional optical system, etc. It is therefore possible to measure absorption in a very small region of a specimen with high resolution without picking up scattered light from the surroundings of the measuring point nor other noise light. Thus, the method and apparatus of the present invention are suitable for measurement of a microscopic absorption distribution in an opaque specimen, for example, an organic tissue.

What we claim is:

1. An apparatus for measuring spectral absorption in an opaque specimen, comprising:
   a monochromatic light source capable of varying the wavelength of light emitted therefrom;
   means for dividing the light from said light source into two light beams;
   means for changing the optical path length at a predetermined speed, said optical path length changing means being provided in the optical path of one of said two light beams;
   a scattering specimen means disposed in the optical path of the other light beam for absorbing a portion of said other light beam passing therethrough from a first side of said specimen means to an opposite side before emerging from said opposite side of said specimen means, said emerging light comprising a beam of parallel rays;
   means for combining together highly directional light emerging from said optical path length changing means and said beam of parallel rays (rectilinear component) emerging from said specimen means in a specific direction and projecting the resulting composite light in the same direction; and
   means for converting the composite light from said beam combining means into an electric signal and detecting the intensity of only an AC component of a frequency corresponding to the optical path length changing speed so as to measure the Spectral absorption of said specimen means.

2. The measuring apparatus of claim 1, further comprising means for cutting off light from said scattering specimen such that the intensity of highly directional light emerging from said optical path length changing means is detected to obtain a reference light intensity, and wherein said means for converting light obtained from said beam combining means converts light into an electric signal and an AC component which is equal to an AC component of a frequency corresponding to the optical path length changing speed which is defined as a signal intensity obtained from said specimen, thereby obtaining a transmission integral extinction by use of said reference light intensity and said signal intensity.

3. An apparatus for measuring a microscopic absorption distribution in an opaque specimen, comprising:
   a monochromatic light source capable of varying the wavelength of light emitted therefrom;
   means for dividing the light from said light source into two light beams;
   means for shifting the frequency of incident light, said shift means being provided in the optical path of one of said two light beams;
   a confocal optical system comprising two convergent optical systems, said confocal optical system being disposed in the other optical path;
   a specimen disposed at a position where light is condensed by said confocal optical system, said specimen being capable of being scanned relative to said confocal optical system;
   means for combining together highly directional light emerging from said frequency shift means and light diverging from a measuring point on said specimen and converted into parallel rays by said confocal optical system and projecting the resulting composite light in the same direction; and
   means for converting the composite light from said beam combining means into an electric signal and detecting the intensity of only an AC component which is equal to the shifted frequency.

4. An apparatus for measuring a microscopic absorption distribution in an opaque specimen, comprising:
   a monochromatic light source capable of varying the wavelength of light emitted therefrom;
   means for dividing the light from said light source into two light beams;
   means for changing the optical path length at a predetermined speed, said optical path length changing means being provided in the optical path of one of said two light beams;
   a confocal optical system comprising two convergent optical systems, said confocal optical system being disposed in the other optical path;
   a specimen disposed at a position where light is condensed by said confocal optical system, said specimen being capable of being scanned relative to said confocal optical system;
   means for combining together highly directional light emerging from said optical path length changing means and light diverging from a measuring point on said specimen and converted into parallel rays by said confocal optical system and projecting the resulting composite light in the same direction; and
   means for converting the composite light from said beam combining means into an electric signal and detecting the intensity of only an AC component of a frequency corresponding to the optical path length changing speed.

5. An apparatus for measuring a microscopic absorption distribution in an opaque specimen, comprising:
   a monochromatic light source capable of varying the wavelength of light emitted therefrom;
   means for dividing the light from said light source into two light beams;
   means for shifting the frequency of incident light, said shift means being provided in the optical path of one of said two light beams;
   a first convergent optical system disposed in the other optical path to illuminate a very small measuring point on a specimen with condensed light of high directivity;
   a specimen disposed at a position where light is condensed by said first convergent optical system, said specimen being capable of being scanned relative to said first convergent optical system;
   a second convergent optical system arranged to illuminate said specimen with highly directional light emerging from said frequency shift means in the form of the same convergent spherical wave as that obtained from said first convergent optical system;
   means for combining together light emerging from said frequency shift means and light diverging from the measuring point on said specimen and converted into parallel rays by said second convergent optical system and projecting the resulting composite light in the same direction; and
   means for converting the composite light from said beam combining means into an electric signal and detecting the intensity of only an AC component which is equal to the shifted frequency.

6. The measuring apparatus of any one of claims 3, 4 and 5, wherein, with light from said scattering specimen being cut off, the intensity of light emerging from said frequency shift means or said optical path length changing means is detected to obtain a reference light intensity, and light obtained from said beam combining means is converted into an electric signal and an AC component which is equal to the shifted frequency or an AC component of a frequency corresponding to the optical path length changing speed is defined as a signal intensity from said specimen, thereby obtaining a transmission integral extinction by use of said reference light intensity and said signal intensity.

* * * * *